(12) United States Patent
Wernke et al.

(10) Patent No.: US 11,160,498 B2
(45) Date of Patent: Nov. 2, 2021

(54) PROSTHESIS AND ORTHOSIS SLIP DETECTION SENSOR AND METHOD OF USE

(71) Applicant: University of South Florida, Tampa, FL (US)

(72) Inventors: Matthew Michael Wernke, Columbus, OH (US); Samuel Lon Phillips, Seminole, FL (US); Derek James Lura, Tampa, FL (US); Stephanie Lutton Carey, Tampa, FL (US); Rajiv V. Dubey, Tampa, FL (US)

(73) Assignee: University of South Florida, Tampa, FL (US)

( * ) Notice: Subject to any disclaimer, the term of this patent is extended or adjusted under 35 U.S.C. 154(b) by 850 days.

(21) Appl. No.: 15/848,233

(22) Filed: Dec. 20, 2017

(65) Prior Publication Data

US 2018/0132786 A1 May 17, 2018

Related U.S. Application Data

(62) Division of application No. 14/082,999, filed on Nov. 18, 2013, now Pat. No. 9,848,822.
(Continued)

(51) Int. Cl.
*A61B 5/00* (2006.01)
*A61F 2/80* (2006.01)
(Continued)

(52) U.S. Cl.
CPC .............. *A61B 5/4851* (2013.01); *A61F 2/70* (2013.01); *A61F 2/76* (2013.01); *A61F 2/80* (2013.01); *A61F 5/01* (2013.01); *A61F 5/0118* (2013.01); *A61F 2002/5036* (2013.01); *A61F 2002/6881* (2013.01); *A61F 2002/704* (2013.01); *A61F 2002/7615* (2013.01); *A61F 2002/7695* (2013.01); *A61F 2002/802* (2013.01); *A61F 2005/0188* (2013.01)

(58) Field of Classification Search
None
See application file for complete search history.

(56) References Cited

U.S. PATENT DOCUMENTS

| | | | |
|---|---|---|---|
| 2008/0147204 A1* | 6/2008 | Ezenwa | A61F 2/7812 623/33 |
| 2012/0153875 A1* | 6/2012 | Glaister | A61F 2/66 318/9 |

OTHER PUBLICATIONS

Sanders et al. "A noncontact sensor for measurement of distal residual-limb position during walking", Journal of Rehabilitation Research and Development, vol. 43, No. 4, pp. 509-516, Jul./Aug. 2006 (Year: 2006).*

* cited by examiner

*Primary Examiner* — Jonathan Cwern
(74) *Attorney, Agent, or Firm* — Smith & Hopen, P.A.; Michele L. Lawson

(57) ABSTRACT

A device and method for measuring prosthetic or orthotic slip is presented. An optical sensor device is attached to the prosthesis or orthosis and measures the amount of relative motion between the prosthetic socket and the residual limb surface or between the orthosis and the affected body part. The sensor device is comprised of an optical sensor, a light source, a processing unit and a power source contained within a housing. A system for measuring multidirectional prosthetic or orthotic slip using the sensor device and automatically adjusting the fit of the prosthetic based on a determined threshold is also presented.

1 Claim, 20 Drawing Sheets

Related U.S. Application Data

(60) Provisional application No. 61/727,249, filed on Nov. 16, 2012.

(51) Int. Cl.
*A61F 2/76* (2006.01)
*A61F 5/01* (2006.01)
*A61F 2/70* (2006.01)
*A61F 2/68* (2006.01)
*A61F 2/50* (2006.01)

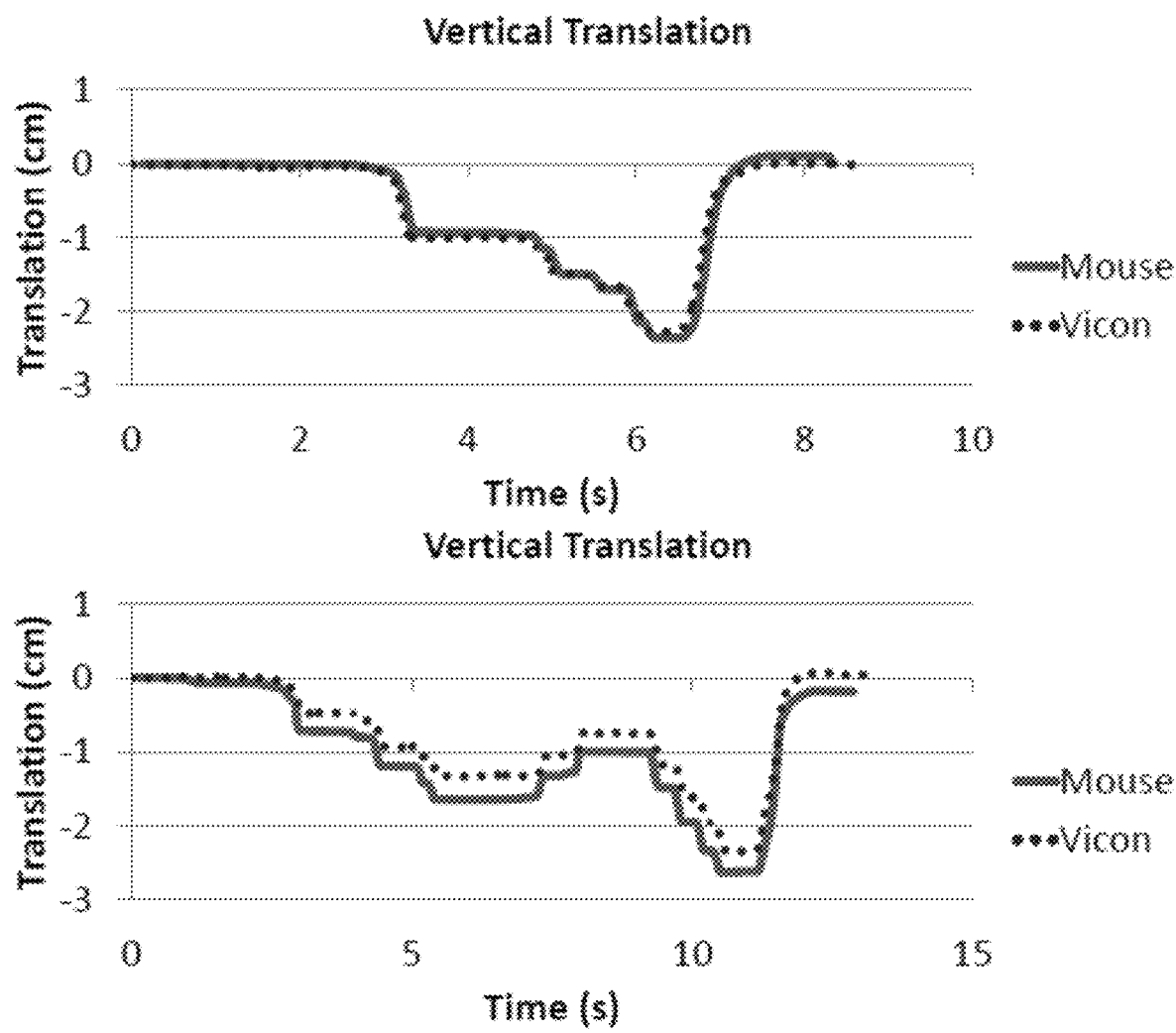
FIG. 15B-C

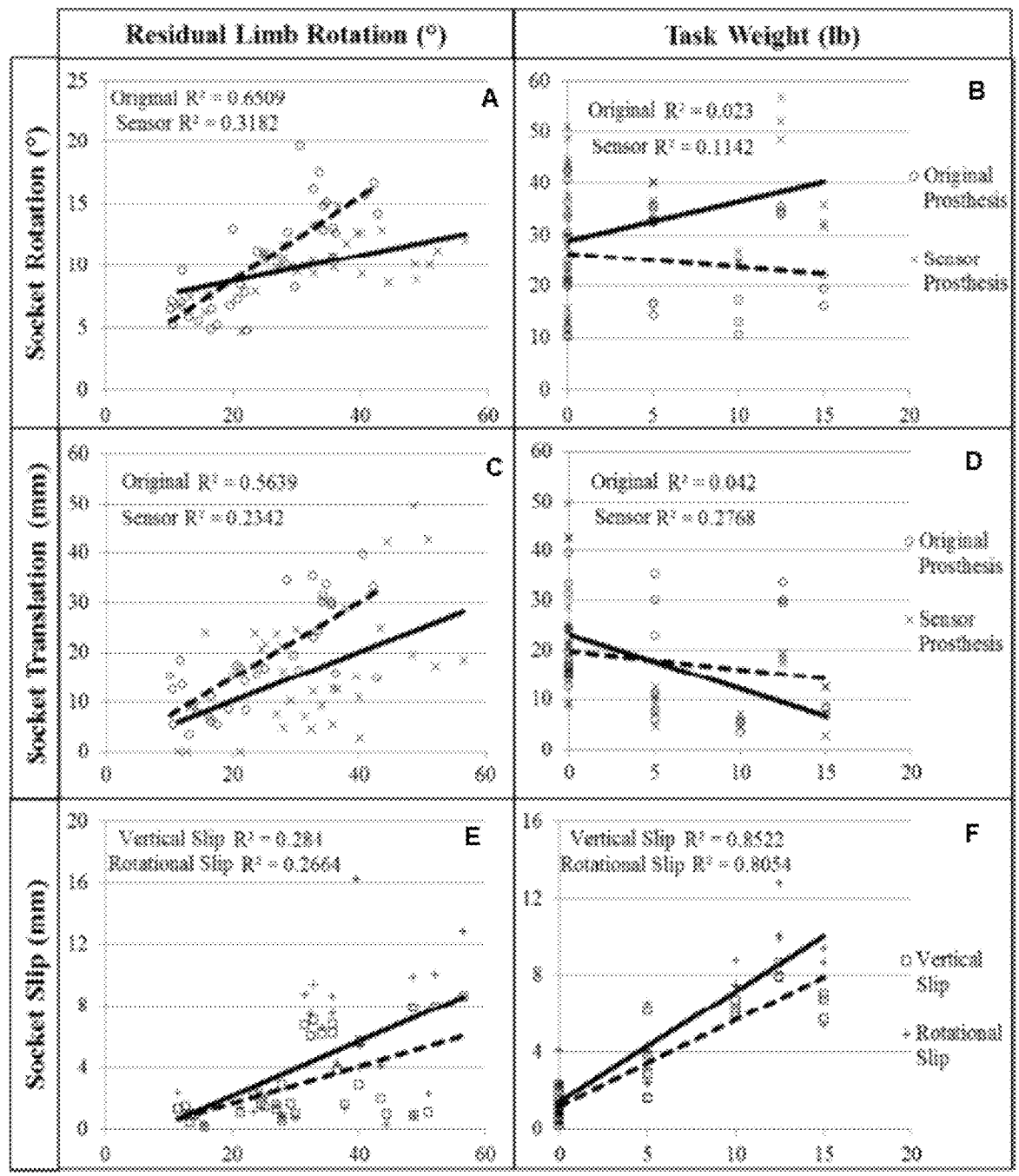
FIG. 18A-F

PROSTHESIS AND ORTHOSIS SLIP DETECTION SENSOR AND METHOD OF USE

CROSS REFERENCE TO RELATED APPLICATIONS

This application is a divisional of and claims priority to U.S. Nonprovisional application Ser. No. 14/082,999, now U.S. Pat. No. 9,848,822, entitled "Prosthesis and Orthosis Slip Detection Sensor and Method of Use", filed on Nov. 18, 2013 which is a nonprovisional of and claims priority to U.S. Provisional Application No. 61/727,249, entitled "Prosthesis and Orthosis Slip Detection Sensor", filed Nov. 16, 2012, the entire contents of which are incorporated herein by reference.

GOVERNMENTAL SUPPORT

This invention was made with Government support under Grant No. W81XWH-10-1-0601 awarded by the U.S. Army Medical Research & Material Command (USAMRMC) and the Telemedicine & Advanced Technology Research Center (TATRC). The Government has certain rights in the invention.

FIELD OF INVENTION

This invention relates to devices for use with prosthetics and orthoses. Specifically, the invention provides an optical sensor device that is used to measure the amount of relative motion (slip) between the prosthetic socket and the residual limb surface or in the case of orthoses, measuring the amount of relative motion between the orthosis and the affected body part.

BACKGROUND OF THE INVENTION

In 2005, an estimated 1.6 million persons living in the United States had a limb amputation, with an expected increase in this population reaching 2.2 million by 2020. (Ziegler-Graham, K., MacKenzie, E. J., Ephraim, P. L., Travison, T. G. & Brookmeyer, R. Estimating the prevalence of limb loss in the United States: 2005 to 2050. *Arch. Phys. Med. Rehabil.* 89, 422-429 (2008)) Data reported by the Joint Theater Trauma Registry and Military Amputee Research Program showed that between October 2001 and June 2006, 423 service members suffered one or more major limb amputation. (Ziegler-Graham, K., et al., *Estimating the prevalence of limb loss in the United States:* 2005 to 2050. Archives of physical medicine and rehabilitation, 2008. 89(3): p. 422-429) In 2010 it was reported that 950 soldiers sustained combat-related amputations and in 2012 it had risen to 1599 from all recent conflicts. (Stinner, D. J., et al., *Prevalence of Late Amputations During the Current Conflicts in Afghanistan and Iraq.* Military Medicine, 2010. 175(12): p. 1027-1029; Fischer, H. U.S. Military Casualty Statistics: Operation New Dawn, Operation Iraqi Freedom, and Operation Enduring Freedom. (2012)).

The prosthetic socket is intended to capture and transfer movements of the residual limb (RL) to the prosthesis. This is challenging, especially for RLs with a high soft tissue to bone ratio. Soft tissues are not suited to be mechanical load bearers, and excessive forces and motions can have damaging effects and diminish the efficacy of the prosthesis. (Dudek N L, Marks M B, Marshall S C and Chardon J P. Dermatologic conditions associated with use of a lower-extremity prosthesis. *Archives of physical medicine and rehabilitation.* 2005; 86: 659-63; Highsmith M J, Highsmith J T and Kahle J T. Identifying and Managing Skin Issues With Lower-Limb Prosthetic Use. in *Motion January/February.* 2011; 21: 41-3) The socket serves as the interface between the human and prosthesis and is important in the comfort and acceptance of the prosthesis. Previous studies have found motion occurs at the interface of both models and a practical setting (Wernke, BMES Conference 2011, Poster; Highsmith, JPO July 2007, Vol. 19, Issue 3, 84-90). A survey of prosthesis users found that socket interface comfort was rated the most important factor and 18.4% report being fit with a new prosthesis at least once a year. (Schultz A E, Baade S P and Kuiken T A. Expert opinions on success factors for upper-limb prostheses. *Journal of Rehabilitation Research and Development.* 2007; 44: 483; Pezzin L E, Dillingham T R, MacKenzie E J, Ephraim P and Rossbach P. Use and satisfaction with prosthetic limb devices and related services. *Archives of physical medicine and rehabilitation.* 2004; 85: 723-9)

Some military service members place particularly high demands on their prosthesis and many are dissatisfied with the current technology. In fact, after noticing a ceiling effect on the amputee mobility predictor, the Comprehensive High Level Activity Mobility Predictor (CHAMP) was developed. (Gaunaurd, I. The Comprehensive High-level Activity Mobility Predictor (CHAMP): A Performance-based Assessment Instrument to Quantify High-level Mobility in Service Members with Traumatic Lower Limb Loss. *Open Access Diss.* (2012)). Further, the complexity of recent military amputees is greater than in the past. Gailey found an increased incidence of other combat associated injuries and more surgeries after limb loss (Gailey, R. et al. Unilateral lower-limb loss: Prosthetic device use and functional outcomes in service members from Vietnam War and OIF/OEF conflicts. *J. Rehabil. Res. Dev.* 47, 317 (2010)).

Limb movement within a prosthesis has been measured in the laboratory, but a practical method for monitoring limb movement is not currently available. Similarly, no efficient method to measure socket slip has been developed which can aid in comparing different models to each other or aid in the fitting process. Thus far, prosthetic socket designs have failed to successfully incorporate active elements.

Socket movement has long been understood as very important to prosthetic fit, but has been difficult to measure. Studies have investigated the movement occurring at the socket interface to better understand socket fit and design. Appoldt rigidly attached a pen to the socket and analyzed the ink trail left on the limb to measure slip, but data had to be analyzed post testing and limited accuracy. (Appoldt F A, Bennett L and Contini R. The results of slip measurements in above-knee suction sockets. *Bull Prosthet Res Fall.* 1968: 106-12)

As methods have improved, more movement has been detected. A variety of radiologic methods have been used including X-ray, fluoroscopy, and Dynamic Roentgen Stereo Photogrammetric Analyses (DRSA) scanning. These methods are limited in their field of view, expose the subject to ionizing radiation and are not practical for use outside of the clinic. For example, Commean measured slip using x-ray by placing lead markers on the skin surface and inner wall of the socket, but was limited to static poses. (Commean P K, Smith K E and Vannier M W. Lower extremity residual limb slippage within the prosthesis. *Archives of physical medicine and rehabilitation.* 1997; 78: 476-85) Motion from roentgengraphic applications showed bone movement relative to the socket between 22 mm and 36 mm. (Lilja, M., Johansoon, T. & Oberg, T. Movement of the tibial end in a PTB prosthesis socket: a sagittal X-Ray study of the PTB prosthesis. *Prosthet. Orthot. Int.* 17, 21-26 (1993); Narita, H., Yokogushi, K., Shii, S., Kakizawa, M. & Nosaka, T. Suspension effect and dynamic evaluation of the total surface bearing (TSB) trans-tibial prosthesis: a comparison with the patellar tendon bearing (PTB) trans-tibial prosthesis. *Prosthet. Orthot. Int.* 21, 175-178 (1997)). Computed tomography was used and found movement of 10 mm under static loading conditions. (Commean, P. K., Brunsden, B. S., Smith, K. E. & Vannier, M. W. Below-knee residual limb shape change measurement and visualization. *Arch. Phys. Med. Rehabil.* 79, 772-782 (1998)). DRSA used during stepping tasks showed up to a 16 mm translation of the socket, however the DRSA viewing window is not large enough to accommodate walking. (Papaioannou, G., Mitrogiannis, C., Nianios, G. & Fiedler, G. Assessment of Internal and External Prosthesis Kinematics during Strenuous Activities Using Dynamic Roentgen Stereophotogrammetric Analysis. *J. Prosthetics Orthot.* 22, 91-105 (2010)). As illustrated above, motion analysis is time consuming and movement can still be difficult to access. (Gholizadeh, H. et al. Transtibial prosthetic socket pistoning: Static evaluation of Seal-In® X5 and Dermo® Liner using motion analysis system. *Clin. Biomech. Bristol Avon* (2011); Highsmith, M. J., Carey, S. L., Koelsch, K. W., Lusk, C. P. & Maitland, M. E. Kinematic Evaluation of Terminal Devices for Kayaking With Upper Extremity Amputation. *J. Prosthetics Orthot.* 19, 84-90 (2007)).

The bone position relative to the socket has also been measured using radiological, acoustic, optical, and marker-based motion analysis techniques to quantify socket movement. (Soderberg B, Ryd L and Persson B M. Roentgen stereophotogrammetric analysis of motion between the bone and the socket in a transtibial amputation prosthesis: a case study. *JPO: Journal of Prosthetics and Orthotics.* 2003; 15: 95; Grevsten S and Erikson U. A roentgenological study of the stump-socket contact and skeletal displacement in the PTB-Suction Prosthesis. *Upsala Journal of Medical Sciences.* 1975, 80: 49-57; Kahle J T. A case study using fluoroscope to determine the vital elements of transfemoral interface design. *JPO: Journal of Prosthetics and Orthotics.* 2002; 14: 121; Lilja M, Johansson T and Öberg T. Movement of the tibial end in a PTB prosthesis socket: a sagittal X-ray study of the PTB prosthesis. *Prosthetics and Orthotics International.* 1993; 17: 21-6; Papaioannou G, Mitrogiannis C, Nianios G and Fiedler G. Assessment of amputee socket-stump-residual bone kinematics during strenuous activities using Dynamic Roentgen Stereogrammetric Analysis. *Journal of biomechanics.* 2010; 43: 871-8; Convery P and Murray K. Ultrasound study of the motion of the residual femur within a trans-femoral socket during gait. *Prosthetics and Orthotics International.* 2000; 24: 226-32; Sanders J E, Karchin A, Fergason J R and Sorenson E A. A noncontact sensor for measurement of distal residual-limb position during walking. *Journal of Rehabilitation Research and Development.* 2006; 43: 509; Gholizadeh H, Osman N, Kamyab M, Eshraghi A, Abas W and Azam M. Transtibial prosthetic socket pistoning: Static evaluation of Seal-In® X5 and Dermo® Liner using motion analysis system. *Clinical Biomechanics.* 2011; Freilich R. Biomechanical model of transhumeral prostheses. University of South Florida. 2009, Masters Thesis) However, radiological methods limited participants to static positions, acoustic methods required bulky hardware added to the socket, embedded optical sensors have only been used to measure pistoning other aspects of socket movement, and marker-based motion analysis have not determined the position of tissues within the socket. Additionally, these methods could not detect slip occurring between the socket and skin surface.

Sanders developed an optical range sensor to measure the amount of pistoning occurring in lower limb prostheses. (Sanders, J. E., et al., *A noncontact sensor for measurement of distal residual-limb position during walking.* Journal of Rehabilitation Research and Development, 2006. 43(4): p. 509) The study found an average of 41.7 mm of movement during gait but it could not distinguish between slip and soft tissue deformation. (Sanders, J. E., et al., *A noncontact sensor for measurement of distal residual-limb position during walking.* Journal of Rehabilitation Research and Development, 2006. 43(4): p. 509). A photographic method was used for clinical purposes under several static loading conditions with an average translation of the socket/residual limb in the vertical direction shown to be 9 mm. (Gholizadeh, H. et al. A new approach for the pistoning measurement in transtibial prosthesis. *Prosthet. Orthot. Int.* (2011)).

Through various measurements, static loading/unloading produces between 10 mm movement and dynamic loading/unloading during gait more than double that amount of movement. All of these studies were on small sample sizes. None of these existing methods allow for a simple nonintrusive method of measuring socket movement during the course of normal activities.

One explanation for the dissatisfaction with current socket designs is the inability of the socket to adjust to changes in RL volume which can result in poor socket fit. Adjustable interfaces have been developed to address changes in RL volume. In these adjustable interfaces, the user can change the internal conditions to account for changes in the residual limb. The residual limb volume can fluctuate over short time periods throughout the day in response to biological and environmental factors; therefore sockets that maintain one shape or one vacuum pressure may not provide adequate suspension over the course of wearing the prosthesis.

A variety of options exist for the method of suspension of a prosthetic socket. Suspension options include self-suspending, harness, pin locking, or vacuum/suction suspended prostheses. One of the newest sockets offering self-suspension is the High-Fidelity socket designed by Randall Alley. (Alley, R., *Biomechanical Discussion of Current and Emergent Upper-Limb Prosthetic Interface Designs.* The Academy Today, 2009. 5(3); Alley, R. *The High-Fidelity Interface: Skeletal Stabilization through Alternating Soft Tissue Compression and Release.* 2011. Myoelectric Symposium) The socket design features four longitudinal struts that provide a high degree of soft tissue compression, taking hold of the underlying bone more so than traditional sockets. Concurrent with the longitudinal struts are four windows that provide soft tissue relief. The Highfidelity socket design is believed to have better contact with the long bones of the residual limb and limit motion between the user and prosthesis. (*Discussion of Current and Emergent Upper-Limb Prosthetic Interface Designs.* The Academy Today, 2009. 5(3))

The RevoLimb (Technology B. RevoFit: Control Your Comfort. [Cited July 2013]) is another self-suspending socket which incorporates movable panels that can be adjusted by the user via a dial to create a tighter or looser fit thus adjusting socket volume. The RevoLimb is based on the same technology used in the Boa closure system (Boa Technology, Steamboat Springs, Colo.).

With regard to vacuum systems, the SmartPuck (5280 Prosthetics. Introducing SmartPuck. [cited July 2013]) and LimbLogic (WillowWood. The Evolution of LimbLogic Provides Elevated Vacuum in an Easier to Use System. [cited July 2013]) are adjustable vacuum systems that are sealed into the socket. Users of these systems can adjust the vacuum settings inside the socket using an Apple iTouch or Bluetooth fob respectively.

While each of the above systems is adjustable, they each require manual adjustment by the user, since what constitutes a good socket fit is still being investigated. These systems do not represent an actively changing system. Vacuum assisted sockets have been shown to reduce volume fluctuations, but many people with an amputation do not prefer vacuum assisted sockets because of comfort, ease of use, and reduced steps taken. (Sanders, J. E. and S. Fatone, *Residual limb volume change: Systematic review of measurement and management.* J Rehabil Res Dev, 2011. 48(8): p. 949-86; Klute, G. K. et al. Vacuum-assisted socket suspension compared with pin suspension for lower extremity amputees: effect on fit, activity, and limb volume. *Arch. Phys. Med. Rehabil.* 92, 1570-1575 (2011)). While these systems allow for the adjustment of socket fit, the timing and amount of adjustment are controlled by the user. The user may not be able accurately detect and resolve issues with socket fit. For instance, excessive slippage of the socket should be avoided; however, absence of slippage may result in other problems. A study investigating the effects of friction and shear using pig skin found an inverse correlation between the magnitude of shear force and the time until skin breakdown occurred. (Goldstein, B. and J. Sanders, *Skin response to repetitive mechanical stress: a new experimental model in pig.* Archives of physical medicine and rehabilitation, 1998. 79(3): p. 265-272)

The inventors previously studied a pneumatic adjustable socket system designed for upper extremities, herein incorporated in its entirety by reference. [VA RR&D#A9226-R Take home study of an advanced upper limb prosthesis, PI: Resnik] This system reacted to changes in pressure within the pneumatic system to adjust level of air pressure in pneumatic bladders, which subsequently adjusted socket volume. The inventors discovered that changes in pressure could be the result of many things. The inventors also found that it was difficult to discriminate between movement, which they wanted to compensate for, and muscle contraction, which they did not want to compensate for. These results led the inventors to ascertain that a measure of the limb itself was required to provide adequate feedback to a dynamic adjustable socket system.

In order to alleviate the disadvantages of the prior art, the inventors have developed a dynamic socket system which utilizes one or more Slip Detection Sensors (SDS) to provide feedback to improve the comfort and improve adjustments to short and long-term changes of the residual limb as well as a method to capture socket movements using motion analysis to accommodate limited space between the socket trim-lines and the body and approximate residual limb bone position within the socket. (Freilich R. Biomechanical model of transhumeral prostheses. University of South Florida. 2009, Masters Thesis).

The Slip Detection Sensor can directly measure slip between the residual limb and prosthetic socket or orthosis to provide dynamic feedback to adjust the prosthetic socket. The socket system enhances long-term socket performance and fit of prostheses through the development of a flexible socket that uses a novel Slip Detection Sensor, the interface of which is able to detect motions that can damage the soft tissues and adjust the socket or warn the prosthesis user before the injuries occur. While this project is targeted to military service members with amputations it will also benefit veterans and civilians with amputations.

SUMMARY OF INVENTION

The inventors developed a prosthesis Slip Detection Sensor that may be used to measure the amount of relative motion between the prosthetic socket and residual limb surface of both upper and lower limb prosthetic and orthotic devices. The Slip Detection Sensor is comprised of an optical sensor such as an optoelectronic sensor, a light source, a processing unit, and a power source, such as a battery, contained within a housing. The housing may be in one or more parts. In an embodiment, the housing is comprised of a base and a removable cover. This housing ensures the skin surface stays within the focal length of the optoelectronic sensor and provides a point of access through the prosthetic socket wall. The housing also maintains a low profile so its impact on the socket remains low. The Slip Detection Sensor may also have an optical sensor port which is embedded into the socket wall and contains the optical sensor housing containing the optical sensor.

Also presented is a method of determining the amount of multidirectional slip between a prosthetic socket and the residual limb surface using the novel Slip Detection Sensor. The Slip Detection Sensor is positioned in an orifice in the prosthetic socket and measures multidirectional socket slip.

A prosthetic socket system is also presented which is comprised of the Slip Detection Sensor integrated into a prosthetic socket, a suspension system for attaching the prosthetic socket to the residual limb, means connecting the Slip Detection Sensor to the suspension system for changing the interface conditions of the socket on the residual limb in response to feedback received from the Slip Detection Sensor.

The ability to measure prosthetic slip will have a great impact on both upper and lower limb prostheses. This tool can be used as an evaluation tool to compare various socket designs, assist a prosthetist during the socket fabrication stages by providing quantitative feedback, and be employed in smart socket interfaces to monitor the amount of movement and adjust socket settings accordingly. Additionally, the device will open new research possibilities for internal socket dynamics.

In use with orthoses, the device can assist with designing orthotics by providing quantitative feedback and can be used as an evaluation tool to compare various orthosis devices.

BRIEF DESCRIPTION OF THE DRAWINGS

For a fuller understanding of the invention, reference should be made to the following detailed description, taken in connection with the accompanying drawings, in which:

FIG. 15B-C is a series of graphs depicting the results of the least and highest error trials. B) vertical translation and C) vertical translation.

FIG. 18A-F are a series of images depicting correlation plots for the task data. The o's and dotted linear regression line correspond to the original prosthesis data. The x's and solid linear regression line correspond to the Slip Detection Sensor prosthesis data. The boxes and the dotted linear regression line correspond to the vertical slip for the Slip Detection Sensor prosthesis and the plus signs and solid linear regression line correspond to the rotational slip for the Slip Detection Sensor prosthesis.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The inventors have developed a prosthesis Slip Detection Sensor that may be used to measure the amount of relative motion between the prosthetic socket and residual limb surface of both upper and lower limb prosthetic devices. In addition, the Slip Detection Sensor may be used to measure the amount of movement between an orthosis and the affected body part of a subject.

Current research focusing on the prosthetic socket interface is limited in the ability to quantify the relative movement between the residual limb surface and prosthetic socket. Evidence of this type of movement develops on the residual limb in the form of blisters or other skin issues typically found within a socket. The invention described herein allows for the movement between the residual limb surface and prosthetic socket to be recorded through the use of an optical sensor.

Figure 1:
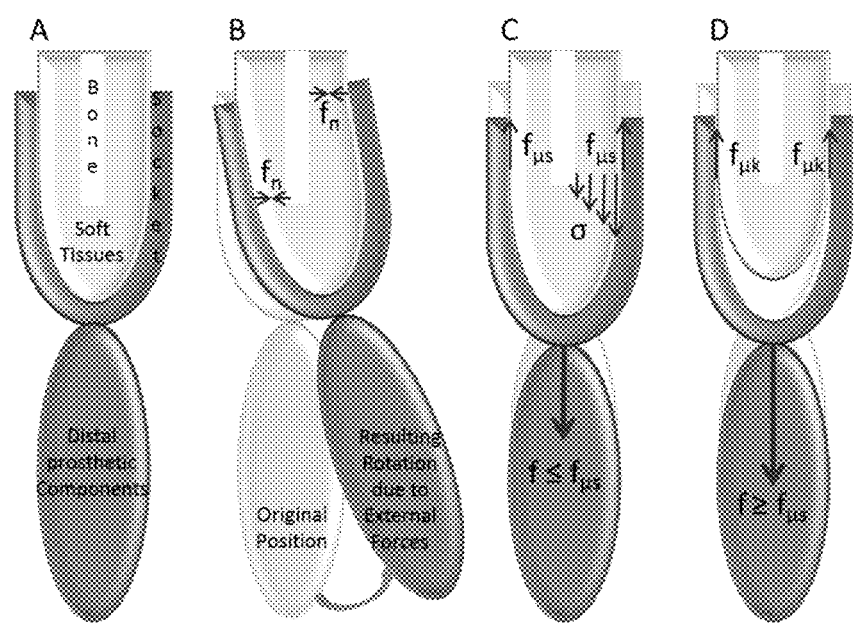
FIG. 1 is an image depicting the general concept of movement within the socket. During volitional movement, forces are transmitted from bone to socket and vice versa. When excessive movement occurs, skin irritation and poor control over the prosthesis can result.

The general concept of movement within a socket is depicted in FIG. 1. During volitional movement, forces are transmitted from bone to socket and vice versa. When excessive movement occurs, skin irritation and poor control over the prosthesis can result.

Figure 2:
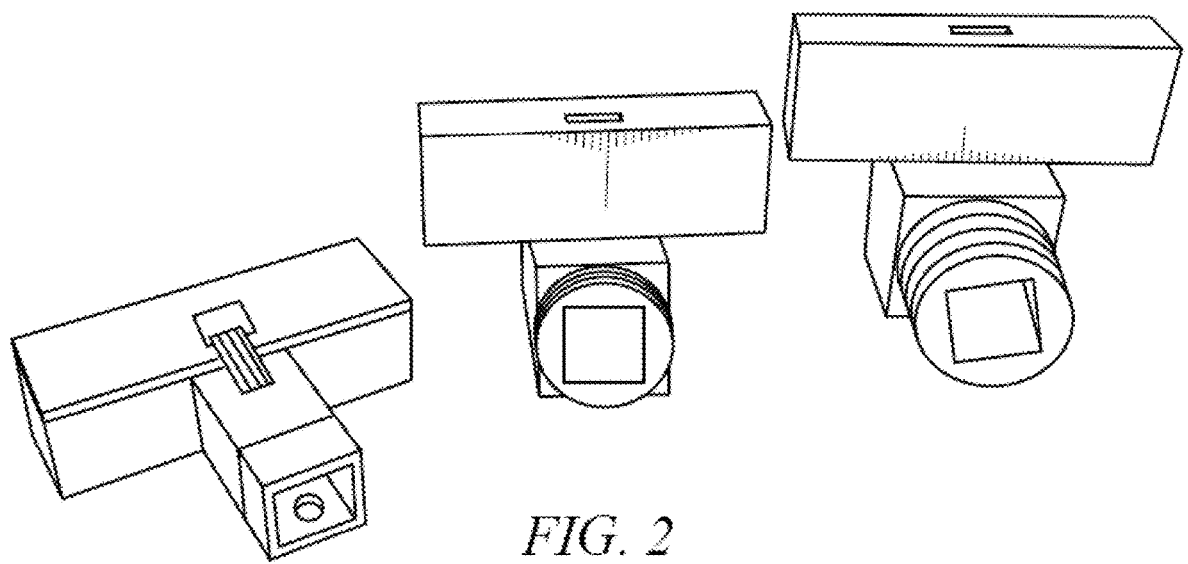
FIG. 2 is a series of images of different embodiments of the prosthetic Slip Detection Sensor.

FIGS. 2-6 illustrate early embodiments of prosthesis Slip Detection Sensor 10. FIG. 2 depicts the first three embodiments of Slip Detection Sensor 10. Embodiment 1 is on the right; embodiment 2 in the middle; and embodiment 3 on the left. As shown in the figure, the size was reduced between the first two embodiments. The design was changed slightly for the third embodiment. The first two embodiments allowed Slip Detection Sensor 10 to translate relative to the circuit board housing. The third embodiment does not contain this feature.

Figure 3:
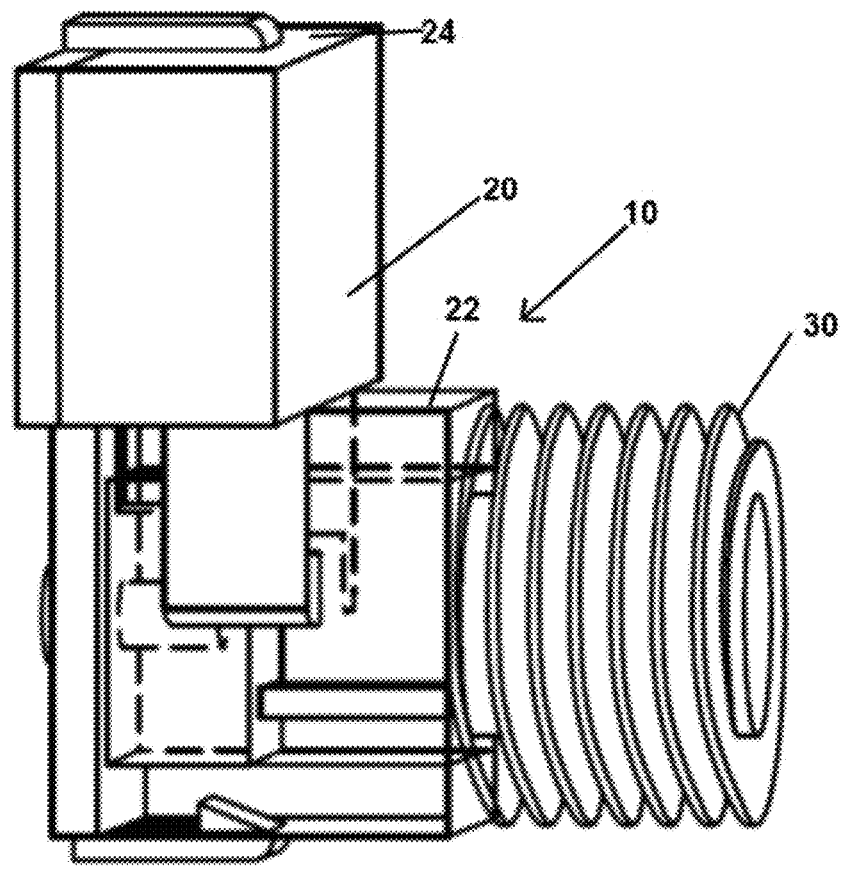
FIG. 3 is an image of one embodiment of the Slip Detection Sensor.

FIG. 3 illustrates the first embodiment of prosthesis Slip Detection Sensor 10 having housing 20 and sensor port 30. In this embodiment, housing 20 is comprised of base 22 and cover 24.

Figure 4:
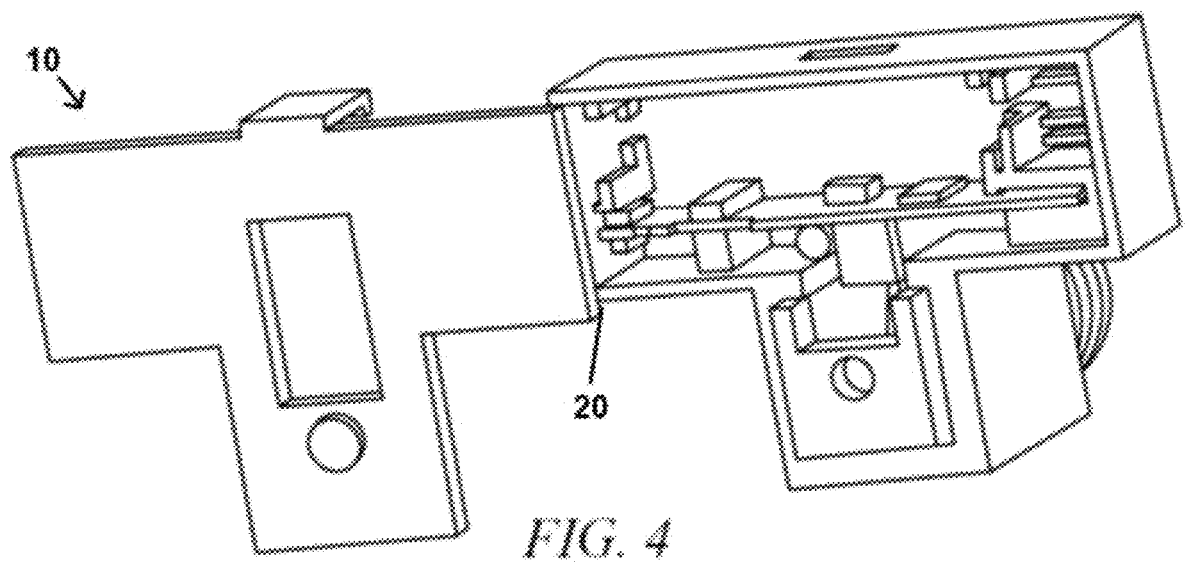
FIG. 4 is an image of a second embodiment of the Slip Detection Sensor.

FIG. 4 illustrates the second embodiment of prosthesis Slip Detection Sensor 10 in which housing 20 is a single unit. The overall size of the device was reduced in this embodiment.

Figure 5:
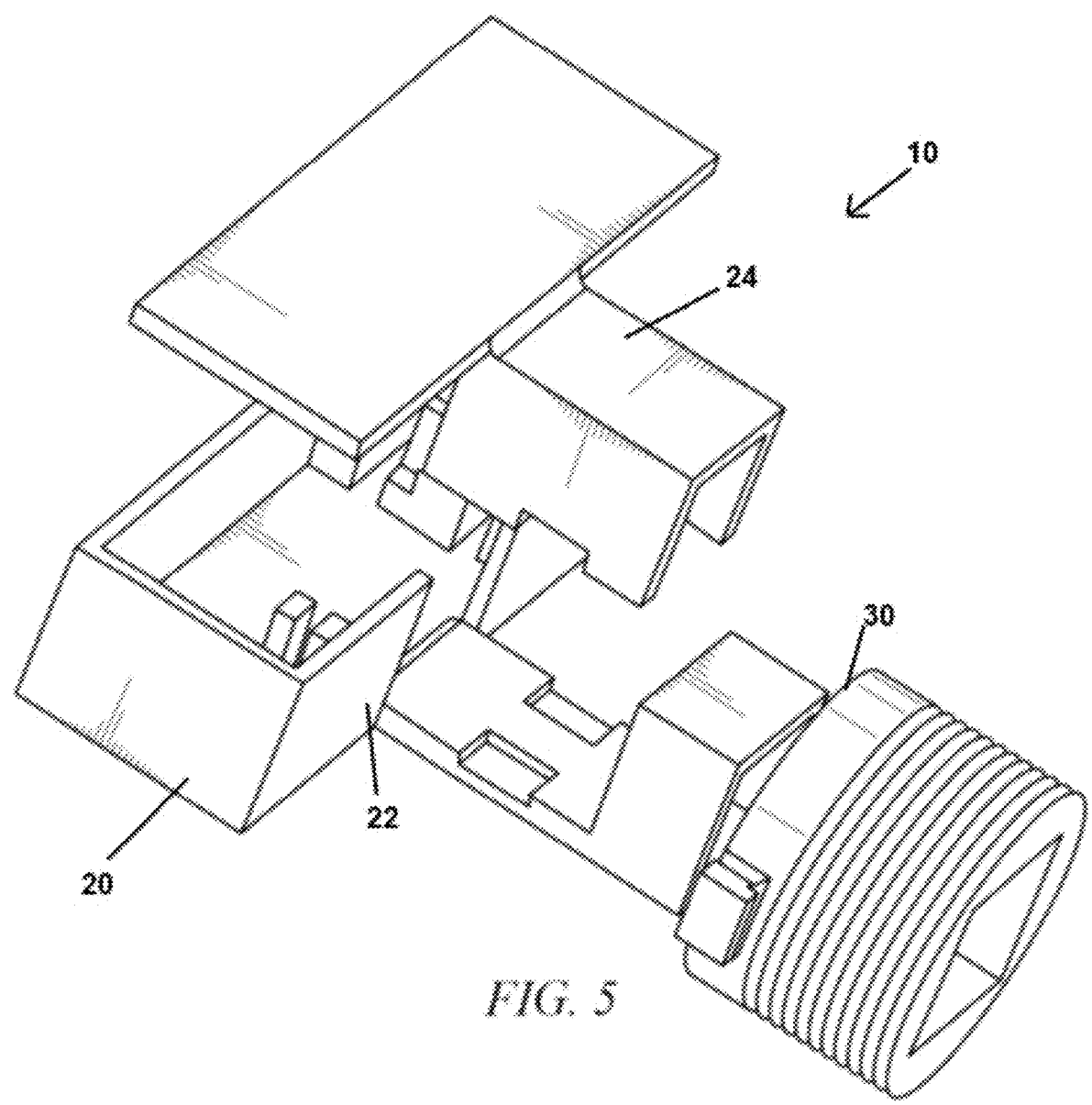
FIG. 5 is an image of a third embodiment of the Slip Detection Sensor.

FIG. 5 is an image of the third embodiment of prosthesis Slip Detection Sensor 10. As shown, the third embodiment is smaller than the previous embodiments. Housing 20 of this embodiment is comprised of base 22 and cover 24. As shown in the image, cover 24 is removable from base 22.

Figure 6:
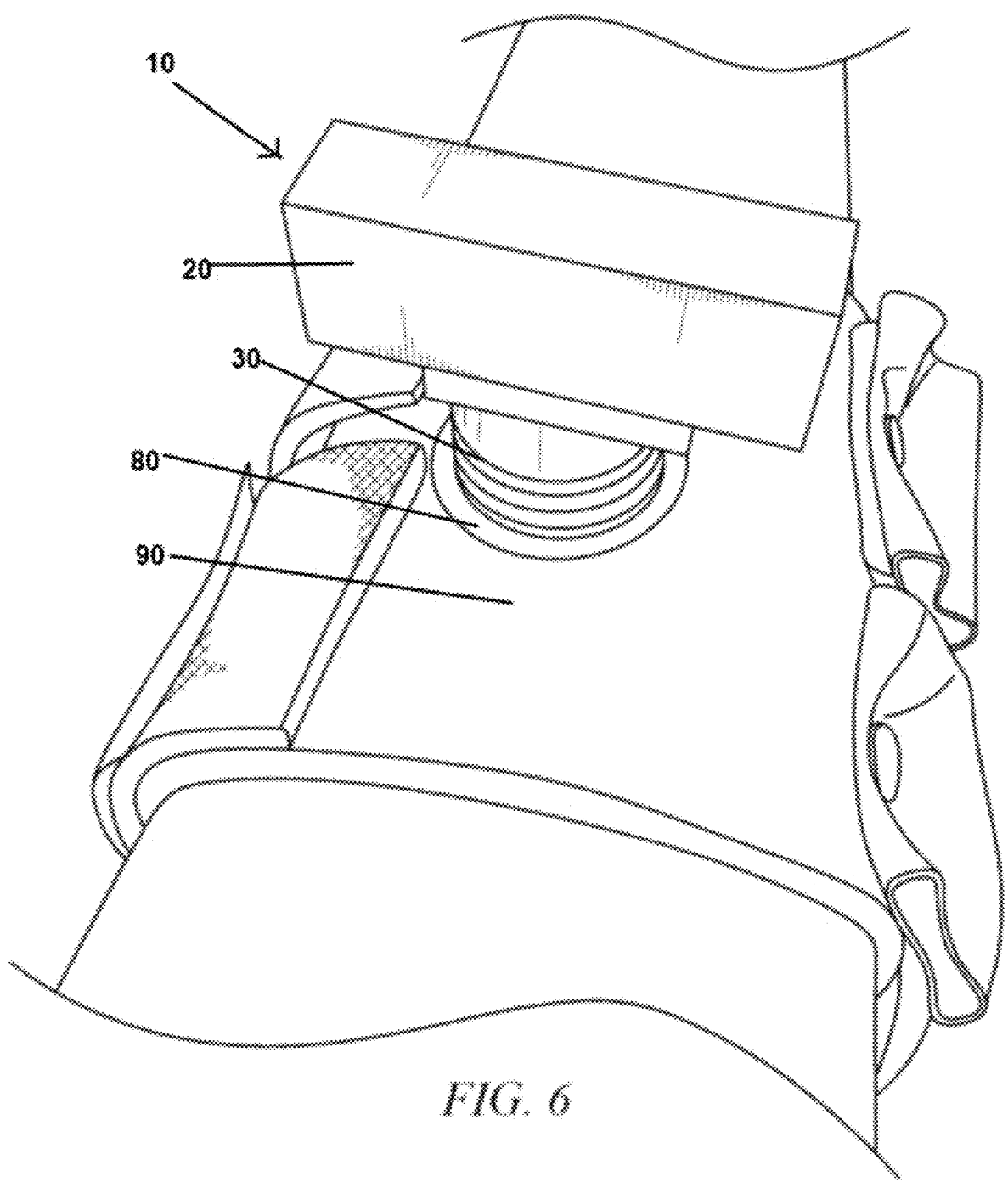
FIG. 6 is an image of the third embodiment of the Slip Detection Sensor in use on a pseudo-prosthesis.

FIG. 6 shows the third embodiment of prosthesis Slip Detection Sensor 10 in use on a pseudo-prosthesis. As shown in FIG. 6, orifice 80 needed to insert Slip Detection Sensor 10 into the socket 90 was still quite large which led to the fourth embodiment of prosthesis Slip Detection Sensor housing 20 shown in FIG. 7.

Figure 7:
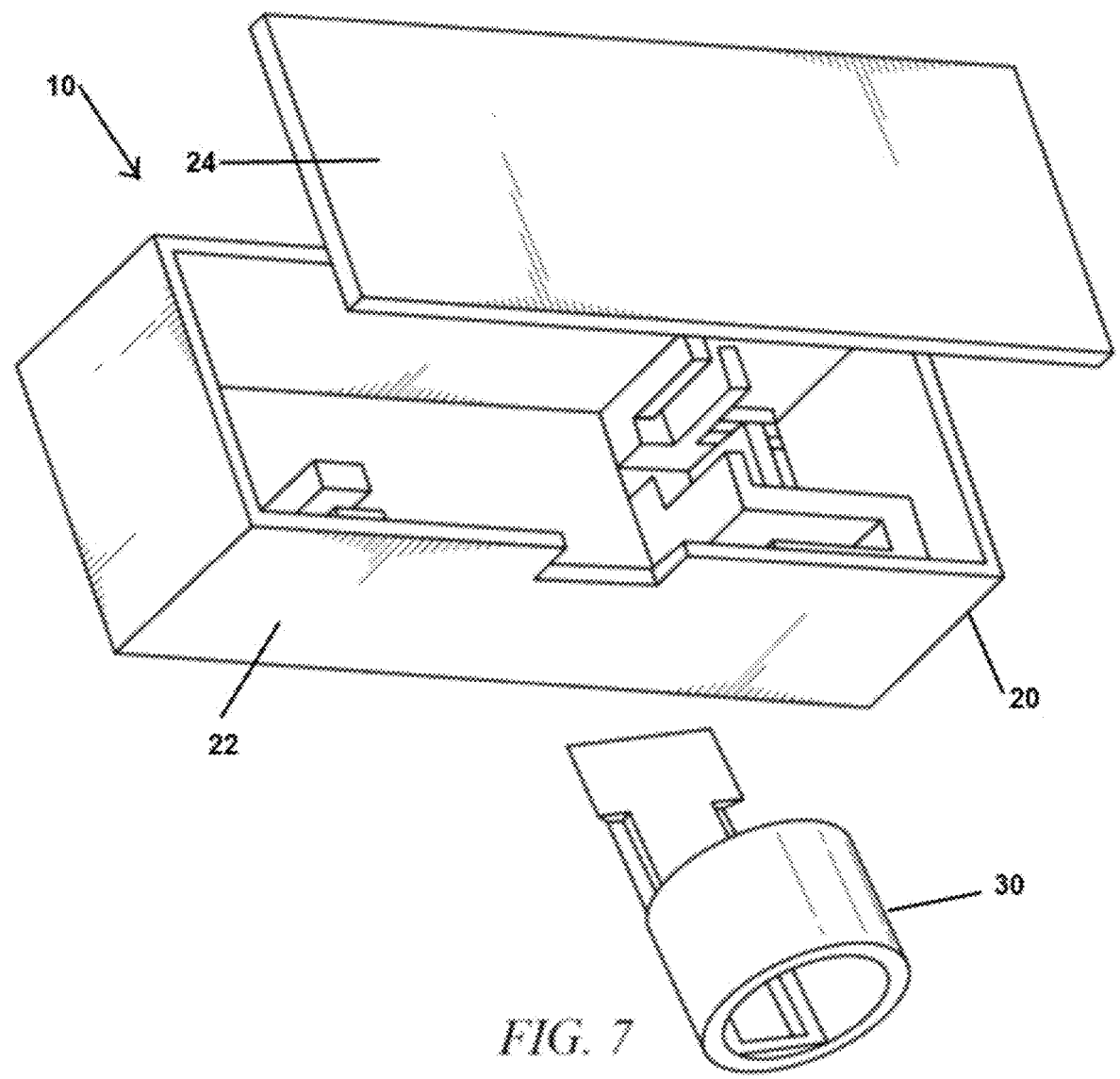
FIG. 7 is an image of a fourth embodiment of the Slip Detection Sensor.
Figure 8:
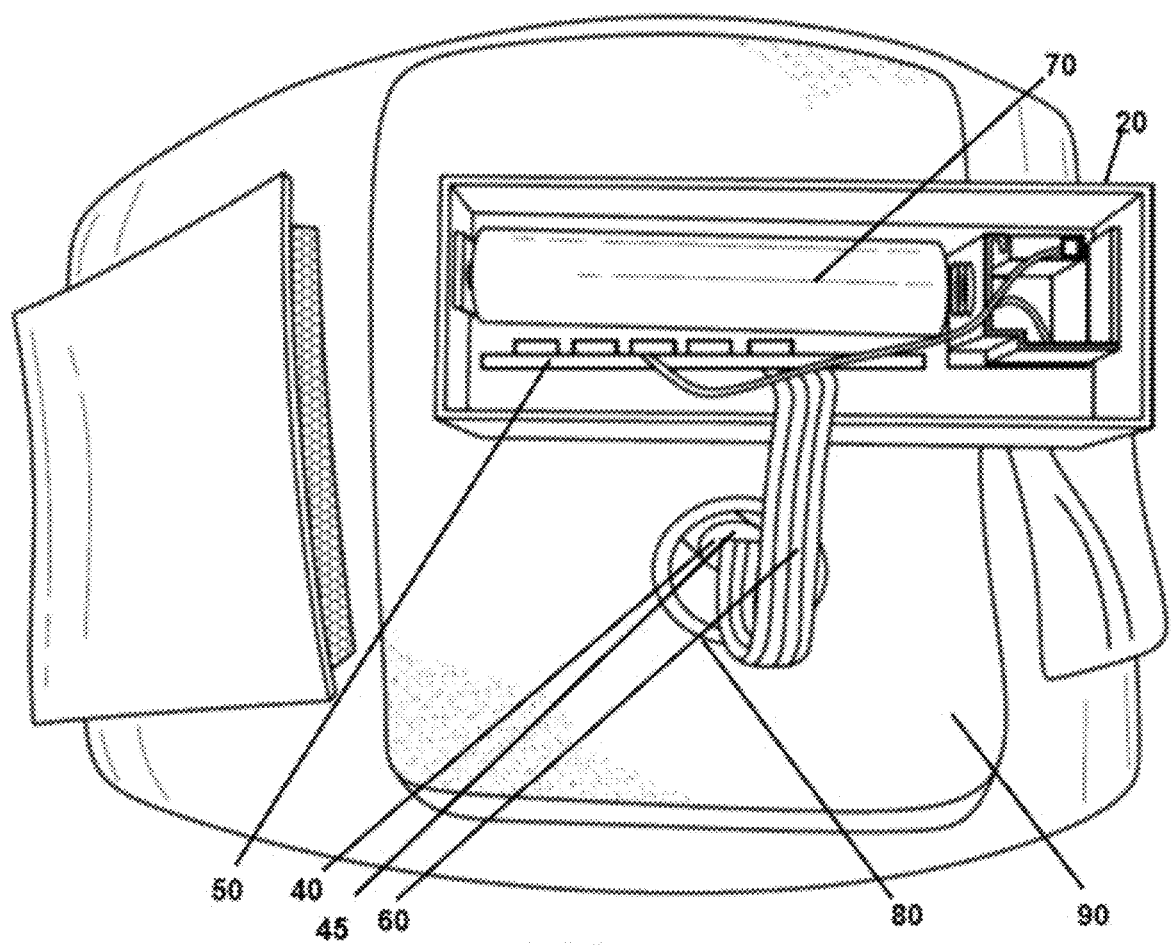
FIG. 8 is an image of the interior of the fourth embodiment of the Slip Detection Sensor showing the power source and circuit board housing.

As illustrated in FIGS. 7 and 8 representing the fourth embodiment of prosthesis Slip Detection Sensor 10, housing 20 is reduced in size from the previous embodiments. This allows Slip Detection Sensor 10 to be less obtrusive to the patient and allows for a smaller diameter sensor port 30 and corresponding orifice 80 in socket 90 to be utilized. As shown in FIG. 7, housing 20 is generally comprised of base 22 and cover 24 where cover 24 removably engages with base 22 to enclose processing unit 50 and power source 70 within housing 20. Base 22 of housing 20 has at least one compartment contained therein to house a power source and a processing unit. Housing 20 may be of an elongated rectangular shape however any shape capable of containing power source and processing unit is contemplated. Base 22 may be comprised of opposing lateral sides. One lateral side may have a substantially circular sensor port 30 removably attached.

FIG. 8 illustrates an interior view of housing 20 when connected to socket 90. Optical sensor 40 and light source 45 is contained within sensor port 30. Optical sensor 40 is connected to processing unit 50 in base 22 via wiring 60. A notch may be positioned in one of the lateral sides of base 22 to allow wiring 60 to extend outward from processing unit 50 and connect to optical sensor 40 which is encased in sensor port 30. In another embodiment, wiring 60 may be fully contained within housing 20. In an embodiment, optical sensor 40 may be an optoelectronic sensor, however other types of optical sensors may be used and are contemplated by this invention. As shown in the figure, power source 70 is electronically connected to processing unit 50 which may be a circuit board. In the embodiment shown in FIG. 8, power source 70 is an alkaline battery but any other type of battery or power source may be used. Battery size may be reduced and the sensor housing and attachment to the prosthetic socket refined and reduced in size. In an embodiment, the device may include a screw threaded port into which the housing may screw into. In an embodiment, software may be upgraded to allow for data collection from multiple sensors simultaneously.

Figure 9:
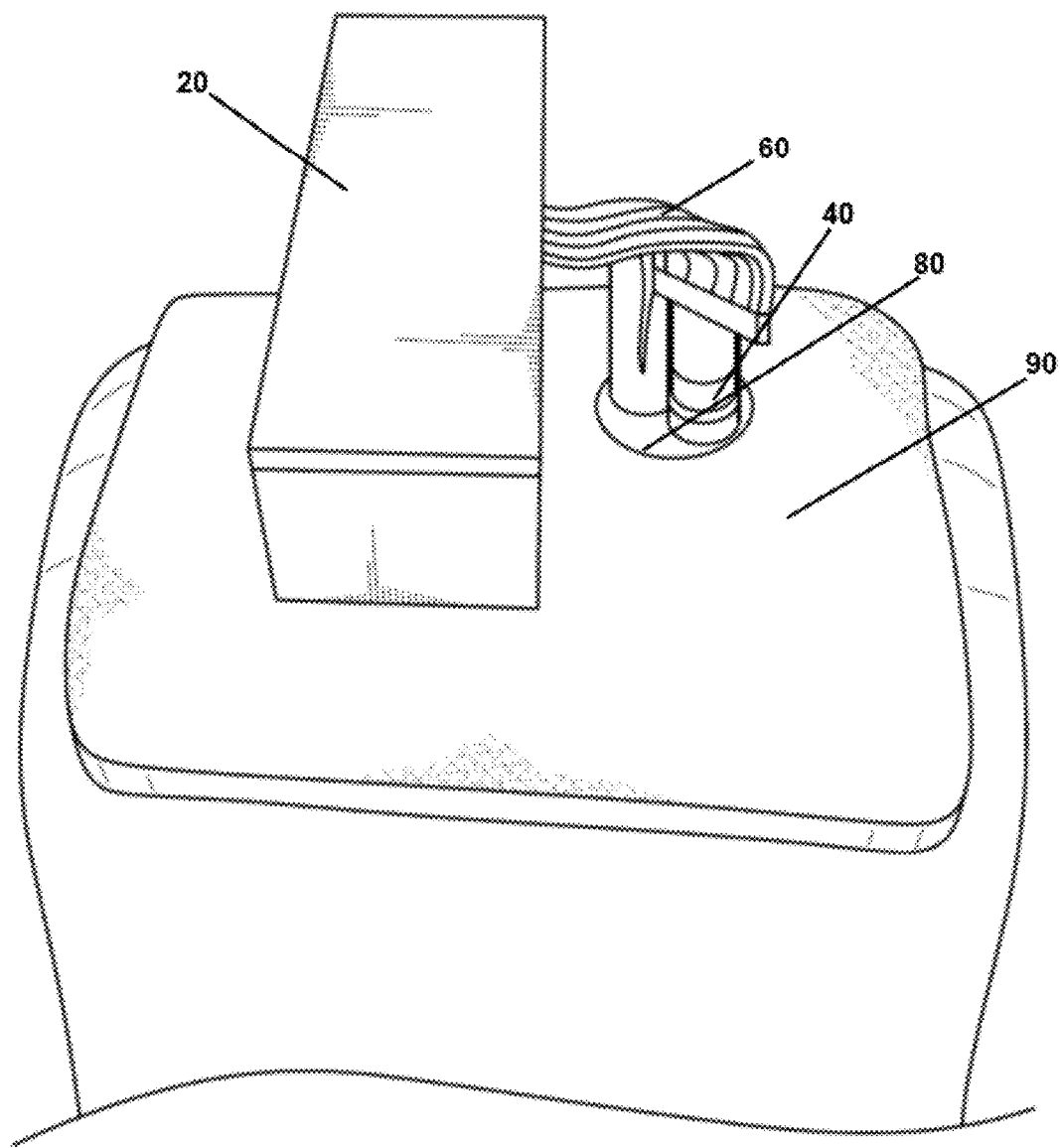
FIG. 9 is an image depicting a side view of the fourth embodiment of the Slip Detection Sensor illustrating the sensor port.
Figure 10:
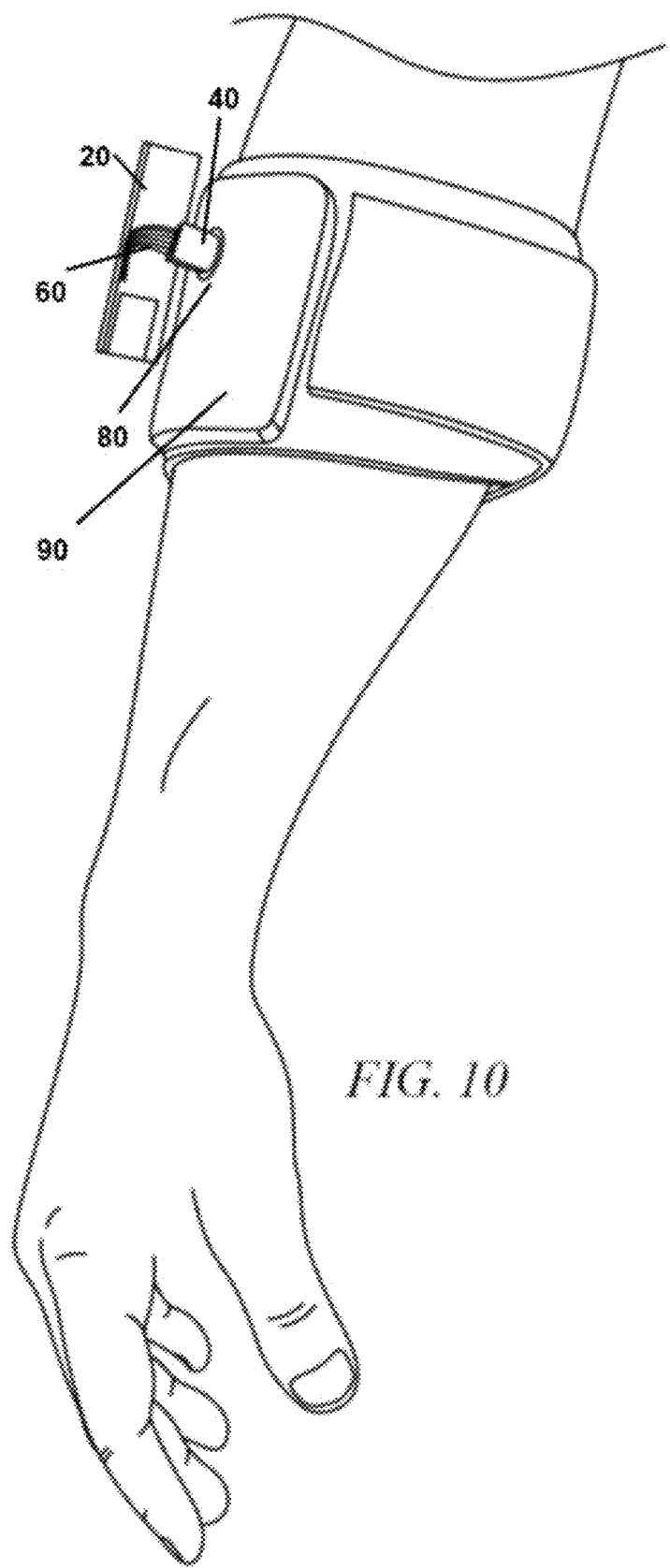
FIG. 10 is an image of the fourth embodiment of the Slip Detection Sensor in use on a pseudo-trans radial prosthesis.
Figure 11:
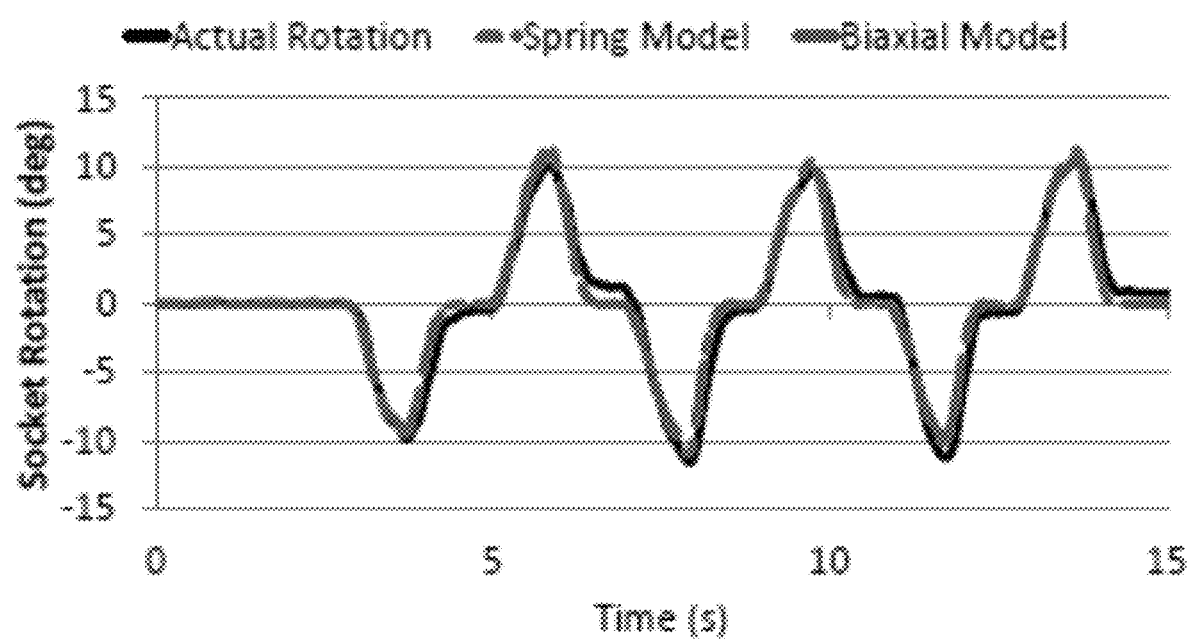
FIG. 11 is a graph depicting ballistic gel model approximations of socket motion, including rotation and slip.
Figure 12:
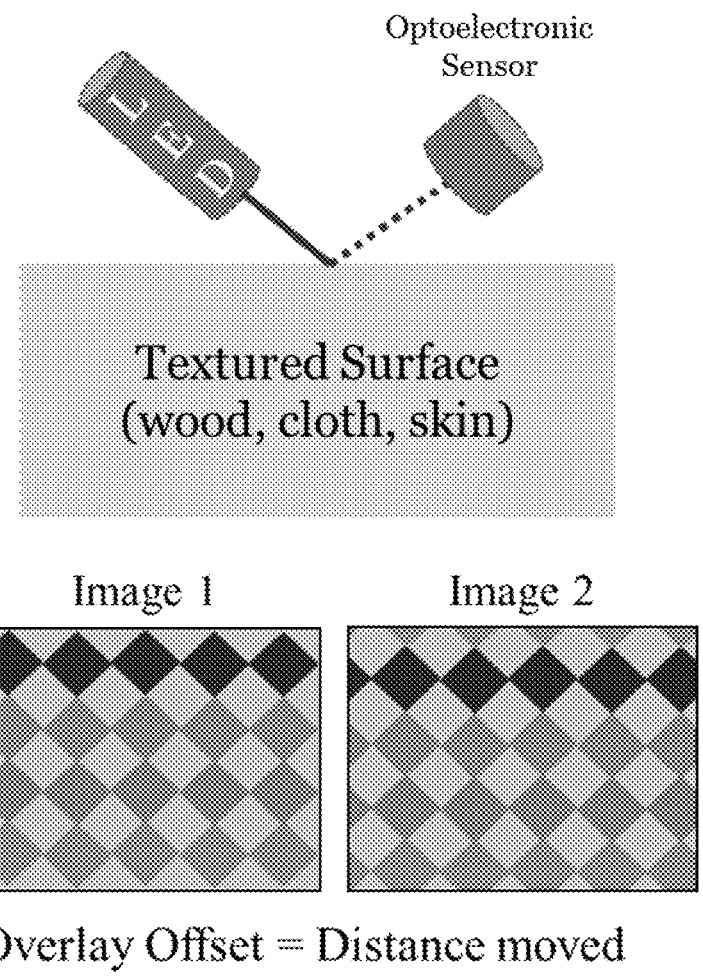
FIG. 12 is a series of images depicting use of the optic sensor. In use, a light source emits light detected by sensor and the offset between image 1 and image 2 determines the distance moved.

As shown in FIGS. 8-10, in use, sensor port 30 containing optical sensor 40 and light source 45 is inserted into orifice 80 present in prosthetic socket wall 90. When sensor port 30 is inserted into orifice 80 of socket wall 90 and housing 20 containing power source 70 and processing unit 50 are attached to sensor port 30, housing 20 abuts socket wall 90. Sensor port 30, as well as corresponding orifice 80 in prosthetic socket wall 90, is preferably of a dimension so as to not be obtrusive while still maintaining complete functionality.

Figure 13:
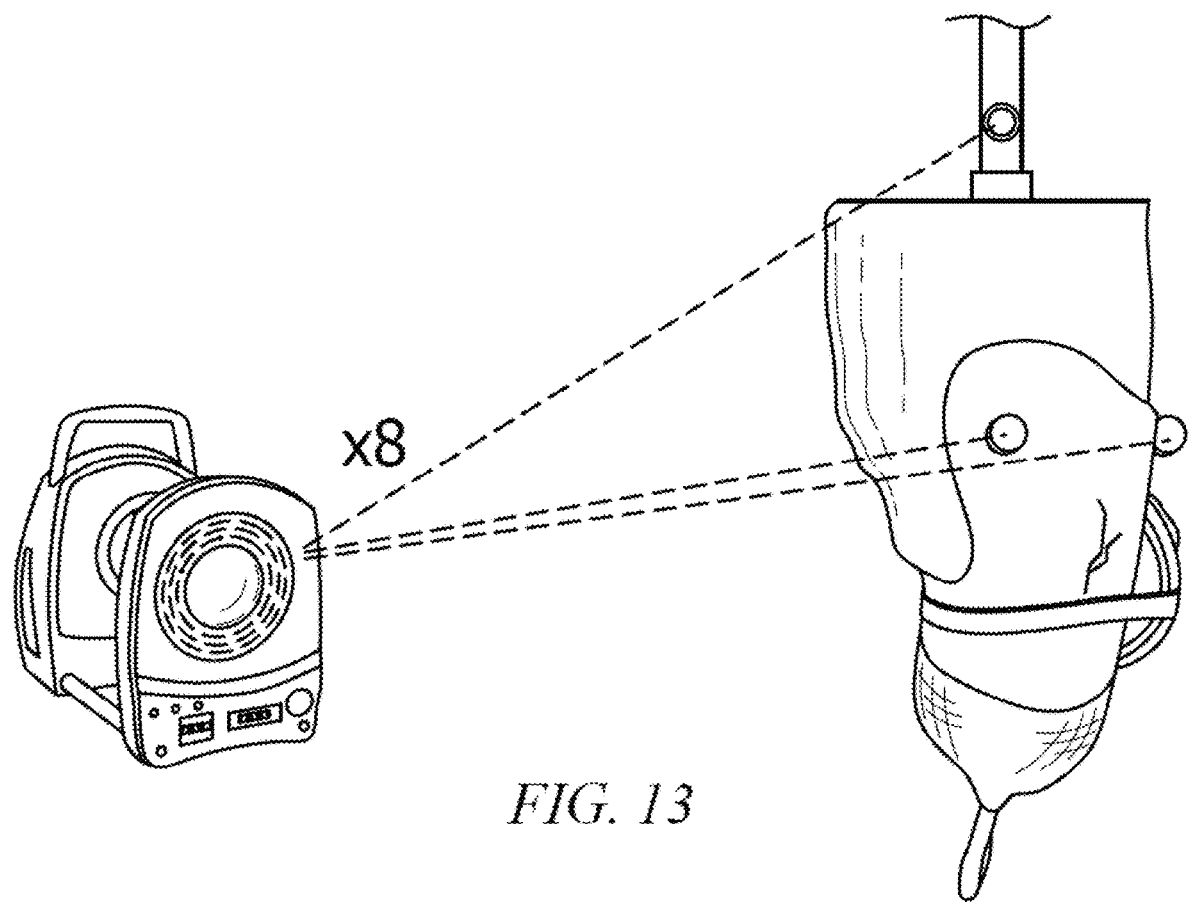
FIG. 13 is an image depicting the tracked marker positions. Results from the Slip Detection Sensor were compared to the results from the Vicon system.

As shown in FIG. 13, a socket with an optical sensor embedded in the wall was placed on a silicon mold of a residual limb and manually translated off the mold then back to the original position using both the Vicon motion analysis system as well as the Slip Detection Sensor (SDS) device.

Figure 14:
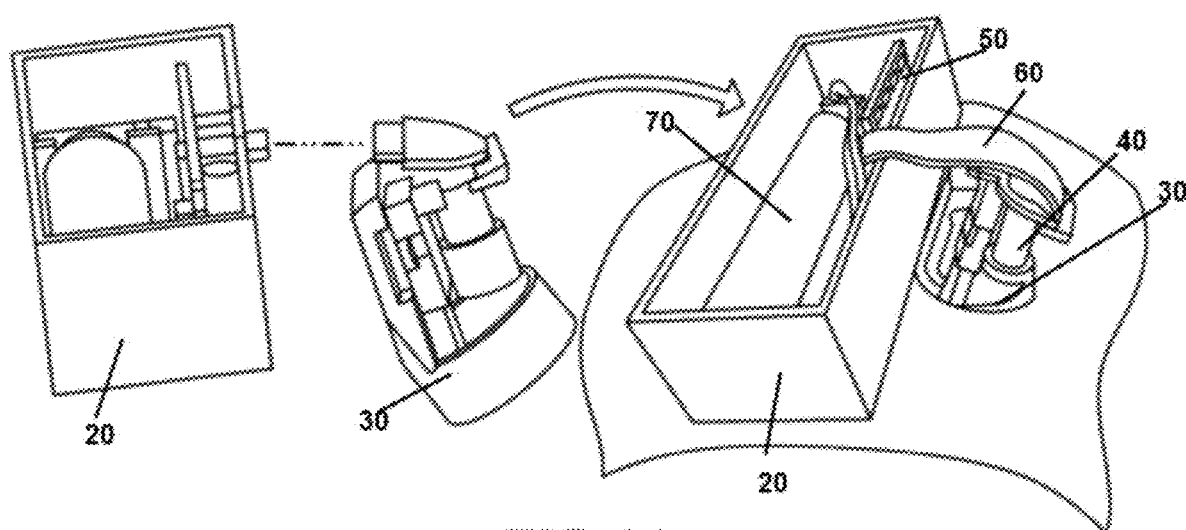
FIG. 14 is an image depicting the optical sensor in use as an actual slip detection sensor in a pseudo socket.

As depicted in FIG. 14, Slip Detection Sensor (SDS) 10 uses an optoelectronic sensor 40 to monitor slippage between the socket 90 and residual limb skin surface or liner. The amount of slip measured by Slip Detection Sensor 10 has been compared to results of a Vicon motion analysis system. An average root mean square error of 0.9 mm was found. The SDS was used in a clinical trial investigating socket movements of above-elbow prosthesis users performing activities of daily living. The data from this clinical trial is used to assess the range of slippage that occurs during common tasks. All sockets in the study are assumed to be a good fit, and the degree to which the participant is satisfied with their socket is verified by the score of their survey responses.

Figure 15A:
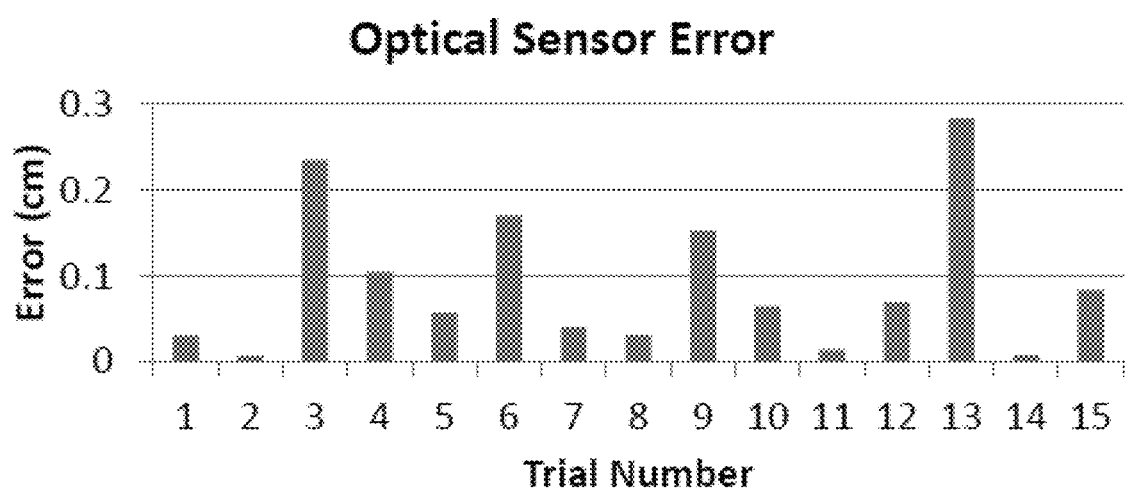
FIG. 15A is a graph depicting the results of the least and highest error trials. A) optical sensor.

The SDS demonstrated a good ability to measure the amount of slip as shown in FIG. 15. A smaller sensor unit reduces the SDS's intrusion into the socket. An optical sensor may be positioned within an amputee's socket to measure the amount of slip during various range of motion and activity of daily living tasks. Having an efficient means of measuring the motion at the socket interface improves the evaluation of existing prosthetic sockets, help create new better designs, and could improve the ability to monitor movement of the socket for advanced suspension systems.

Figure 16:
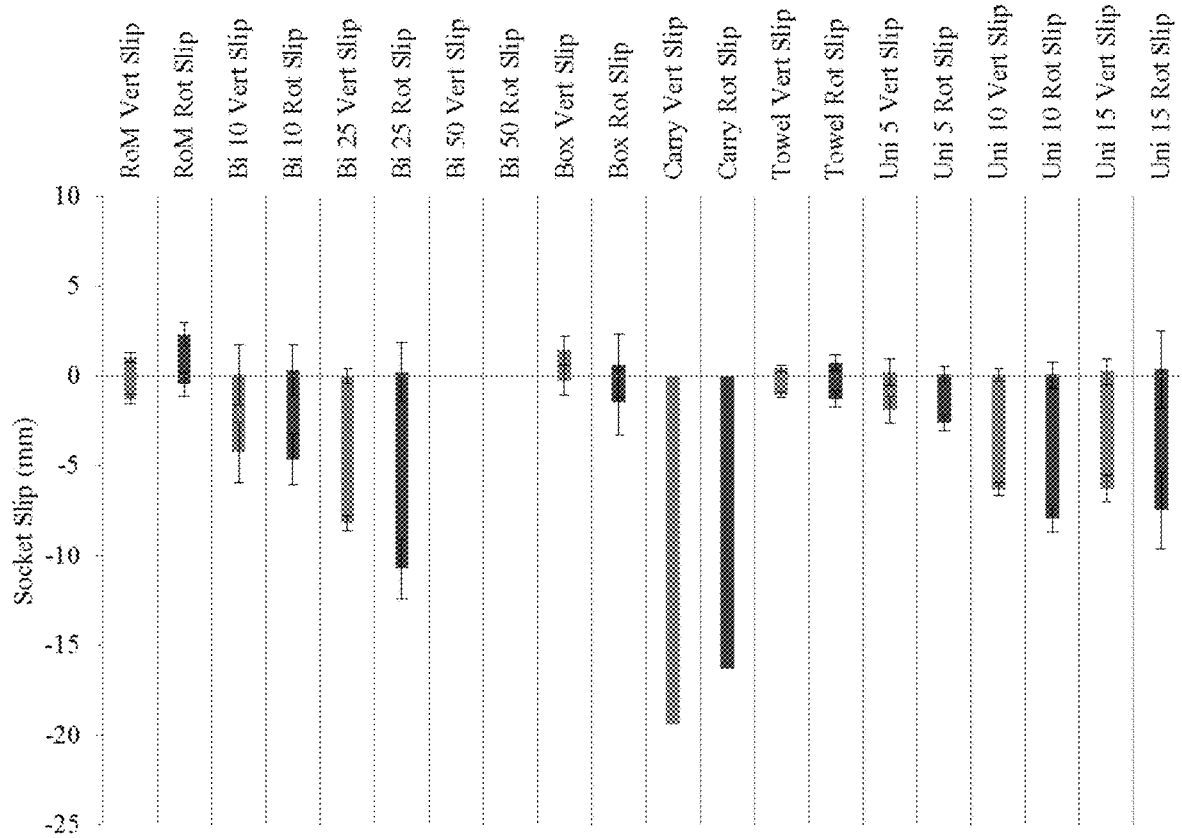
FIG. 16 is an image depicting the Slip Detection Sensor's ability to track socket slip during various tasks.

The Slip Detection Sensor has shown the ability to track socket slip as shown in FIG. 16. The socket slip was largest for the carry trial, where participants held a gallon of milk with their prosthesis while walking. These data highlight the benefits of an adjustable interface. A load applied for a long duration is not properly supported by current socket designs, but a dynamic interface controlled by the Slip Detection Sensor can improve this result by constantly monitoring the interface and adjusting the conditions to limit or eliminate slip motion. Algorithms programmed into the processing unit will constantly sample the multidirectional socket slip data obtained from the SDS over time. Thresholds are programmed into the algorithm and if the amount of slip exceeds these limits then a signal is sent to the suspension system to increase/decrease the settings and automatically adjust the fit of the prosthesis. "Multidirectional socket slip" refers to slip that occurs in the socket and can be measured in all directions.

Figure 17A:
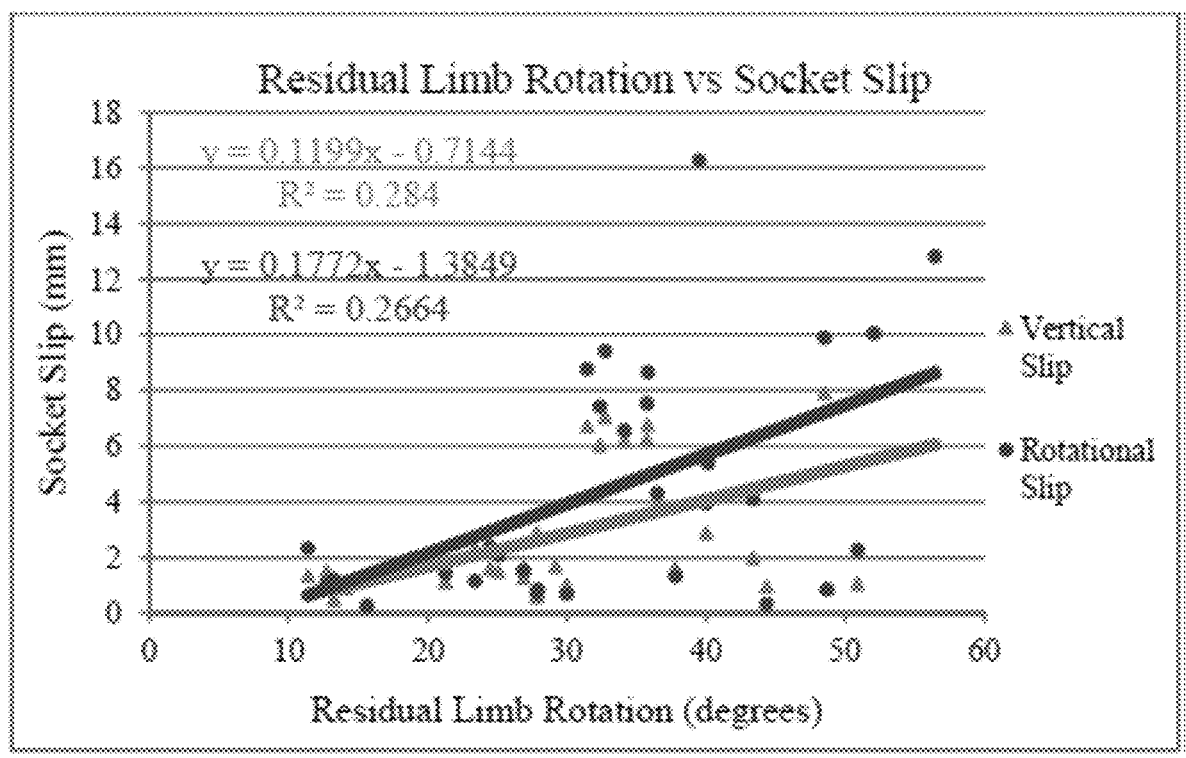
FIG. 17A is an image depicting that the Slip Detection Sensor can detect slip for subjects with transhumeral amputations. The amount of slip correlates to the amount of residual limb rotation and the loading of the terminal device. (A) residual limb rotation vs. socket slip.
Figure 17B:
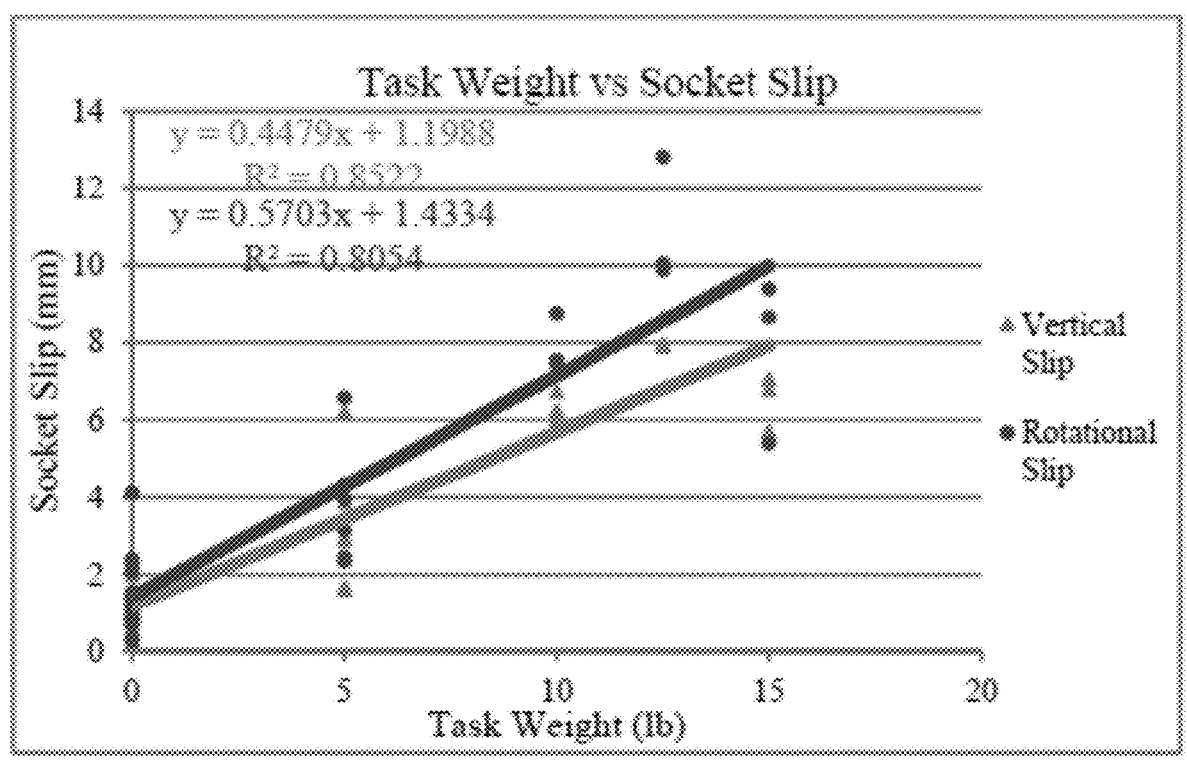
FIG. 17B is an image depicting that the Slip Detection Sensor can detect slip for subjects with transhumeral amputations. The amount of slip correlates to the amount of residual limb rotation and the loading of the terminal device. (B) task weight vs. socket slip.

The inventors have demonstrated that the Slip Detection Sensor can detect slip for subjects with transhumeral amputations as illustrated in Example 1 described below. The amount of slip correlates to the amount of residual limb rotation and the loading of the terminal device as shown in FIGS. 17A and B. Participants were asked to complete a series of tasks with both their original prosthesis and a duplicated prosthesis incorporating the Slip Detection Sensor. Duplication of the original prosthesis was accomplished by making a positive mold of the socket shape using alginate, wrapping the alginate with plaster wraps, and filling that wrap cast with a plaster mixture. A clear thermoplastic socket was blister formed over the plaster mold and the Slip Detection Sensor was attached to the lateral socket wall at a point even with the axilla. The results have been fully analyzed for one of the participants thus far.

Briefly, the participant completed a series of activities of daily living tasks, including folding a towel, a modified box and blocks test, walking and carrying a gallon of water for one minute, a unilateral lifting task at 5, 10, and 15 pounds, and a bilateral lifting task at 10 and 25 pounds. The Slip Detection Sensor results had a strong correlation ($p<0.01$) for the amount of terminal device loading and the amount of residual limb rotation. When analyzing all the correlations, it is clear for this participant that the amount of socket rotations was a function of the residual limb movement, and the amount of socket slip was a function of the amount of terminal device loading. Analysis of more participants is currently underway with similar results expected.

The inventors found, as expected, a greater range of motion (RoM) of the residual limb without wearing a prosthesis than when wearing either of the prostheses. Socket rotation was found to be primarily dependent on the amount of residual limb (RL) rotation while socket slip primarily depended on the task weight. However more socket slip was found for the 25 lbs. bilateral lifting task (12.5 lbs. in the prosthesis) than the 15 lbs. unilateral lifting task, and may be due to the larger degree of movement of the residual limb to complete the bilateral task, which was also found to have a significant effect on socket slip ($p=0.0011$ for vertical slip and $p=0.0015$ for rotational slip). These results were not expected by the inventors, who hypothesized that all movements of the socket relative to the RL would correlate primarily with loading of the terminal device. The study found the range of socket rotation to be about 5 to 20 degrees and the range of socket slip to be about 0 to 1.3 cm for most tasks. The participant rated the original prosthesis an 8/10 in regards to satisfaction, suggesting that he was satisfied with the fit and performance. Additional participants will be analyzed to determine if these results are typical of the range of motion found in satisfactory sockets, and to find a range that could be used to control a dynamic interface.

Reaction from the participant during the testing protocol suggests that the amount of socket slip should be minimized in order to achieve a high performing socket. Minimal socket slip was recorded during the range of motion tasks, and increased as the terminal device loading increased. The Slip Detection Sensor could be a useful tool for quantifying what a range of acceptable socket slip is and a dynamic interface system designed to maintain the acceptable range. The acceptable range is determined by assessing task performance and functional outcome of tasks to ascertain the point at which the amount of slip becomes detrimental to the performance/function of the task. The amount movement can then be assessed and a range of acceptable movement determined. As a non-limiting example, skin damage studies may be used to determine the effects of forces on the skin surface and ascertain the point at which skin breakdown occurs. The movement detected by the SDS can then be correlated to the amount of force that is applied to the soft tissues to determine an acceptable range. The Slip Detection Sensor prosthesis may have allowed more slip than in the participant's original system because the thermoplastic material of the socket may not have created the same suction seal as inner liner material of the original prosthesis. The amount of slip at different points in the socket using multiple Slip Detection Sensors may also be measured.

The harness system may have affected how the socket moved about the RL. Most of the translations captured by the motion analysis system showed the socket moved toward the shoulder joint. While this was not initially hypothesized, movements required to place tension in the cable-driven arm could explain these results. Follow up experiments investigating strain measurement of the harness system as the prosthesis is moved through space are planned.

Example 1 below illustrates socket movement for a transhumeral prosthesis user during activities of daily living (ADL), using motion analysis and an SDS. The data may be used to develop algorithms to provide open or closed loop feedback for a dynamic interface system. These algorithms will constantly sample the multidirectional socket slip over time. Thresholds are programmed into the algorithm and if the amount of slip exceeds these limits then a signal is sent to the suspension system to increase/decrease the settings and automatically adjust the fit of the prosthesis. The data is limited by its approximation of the RL bone position, but any method to confirm its position relative to the motion analysis system would be intrusive. There is also no method to verify the SDS readings. Future work will improve the accuracy of the SDS by developing a more robust tracking algorithm.

Example 1—Transhumeral Amputee

Methods

All procedures were reviewed and informed consent was received prior to data collection. One male (age: 43; height: 174.8 cm; weight: 80.7 kg) transhumeral amputee participated in the case study. His RL measured 26 cm from acromion to distal end and 18 cm from axilla to distal end. His residual limb presented as firm and muscular. The participant regularly uses a body-powered prosthesis with a suction liner and figure-8 harness.

An eight camera Vicon motion capture system and SDS were used to measure the motion of the socket relative to the RL. The motion cameras recorded reflective marker positions at 120 Hz, and the data were used to calculate Euler angles and equivalent axis rotations for the RL and socket segments, and total translation between the RL and socket segments. (Table 1)

TABLE 1

Marker placement descriptions

| Name | Placement |
| --- | --- |
| T1 | Spinous process of $1^{st}$ thoracic vertebrae |
| T10 | Spinous process of $10^{th}$ thoracic vertebrae |
| CLAV | Juguhr notch |
| STRN | Xiphoid process |
| LBAK | Left scapula (used for assymetry) |
| R/LASI | Right/Left anterior superior iliac spine |
| R/LPSI | Right/Left posterior superior iliac spine |
| R/LIC | Right/Left iliac crest |
| R/LSHOA | Right/Left anterior acromion |
| R/LSHOP | Right/Left posterior acromion |
| R/LELB | Right/Left lateral epicondyle |
| R/LELBM | Right/Left medial epicondyle |
| R/LWRA | Right/Left raial styloid |
| R/LWRB | Right/Left ulnar styloid |
| R/LFIN | Right/Left $3^{rd}$ metacarpal head (dorsal side) |
| SCKTA | Anterior socket 10 cm from superior trim lines |
| SCKTP | Posterior socket 10 cm from superior trim lines |

The SDS employed an optoelectronic sensor, similar to a computer mouse, to record the amount of vertical and rotational slip occurring between the skin surface and the socket. The results from the SDS were compared to the motion capture system prior to testing in order to test its calibration. The sensor was mounted to a cuff made of thermoplastic material and moved about the subject's upper arm. An average root mean square error of 1.9 mm was found for all of the trials. Some of this error may be attributed to soft tissue deformation, not slip, detected by the motion capture system and not the SDS. For testing, the SDS was mounted to the lateral edge of the socket wall, at the height of the axilla when the subject's arms were at his side. A duplicate prosthesis was made to incorporate the Slip Detection Sensor.

The socket shape was duplicated by a series of positive and negative molds, first using alginate then using plaster, before blister forming the new socket with thermoplastic. An E400 prefabricated elbow and forearm, quick disconnect wrist assembly, Hosmer hook 5XA, and a thermoforming suction valve were used for the Slip Detection Sensor prosthesis.

Data collection was divided into two days. The first day the participant completed range of motion (RoM) tasks without wearing a prosthesis and the Trinity Amputation and Prosthesis Experience Scales (TAPES). The RoM tasks included shoulder abduction/adduction, flexion/extension, and rotation. During this time, the participant's socket shape was duplicated.

One week later, the participant returned to complete RoM and ADL tasks while wearing the original and Slip Detection Sensor prosthesis. The RoM tasks were the same as day 1 and also included elbow flexion/extension. The ADL tasks included the modified box and blocks test, a towel folding task, bilateral lift tasks (task weights of 10 and 25 lbs.), and unilateral lift tasks (task weight of 5, 10, and 15 lbs.). (Hebert J S and Justin Lewicke M. Case report of modified Box and Blocks test with motion capture to measure prosthetic function. *Journal of Rehabilitation Research and Development.* 2012; 49: 1163-7) A task weight of 0 lbs. was given for all other trials. Each task was repeated three times totaling 33 trials.

Euler angles were used to report the RL, socket, and contralateral limb RoM for the original and Slip Detection Sensor prostheses. The magnitude of RL equivalent axis rotations and task weights were compared to the socket equivalent axis rotation, translation and slip for each task.

Linear regression of correlation plots were used to evaluate the data. The coefficient of determination was used to calculate p-values for statistical analysis.

Results

The participant reported using his prosthesis 6-8 hours a day and rated his prosthesis an 8/10 score in overall satisfaction on the TAPES survey. He rated most aspects as very satisfied, except comfort which he rated as satisfied.

The results of the RoM tasks for upper arm/RL rotation as well as socket rotation and translation are given in Table 2. The contralateral limb had the largest RoM. The difference between the RoM of the original and Slip Detection Sensor prostheses was small, showing the duplication and addition of the SDS did not greatly affect the socket integrity.

TABLE 2

Upper arm and RL rotation, socket rotation and translation from the RoM tasks. Contralateral Upper Arm and Residual Limb Rotations, Socket Rotation and Translation

|  | Abduction (°) | Flexion (°) | Rotation (°) |
| --- | --- | --- | --- |
| Contralateral Upper Arm | 82.46 | 91.59 | 89.24 |
| Residual Limb No Pros | 69.08 | 74.76 | 58.02 |
| Residual Limb Original Pros | 62.19 | 77.74 | 62.99 |
| Residual Limb Duplicate Pros | 68.83 | 73.71 | 64.08 |
| Socket Original Prosthesis | 17.03 | 33.95 | — |
| Socket Duplication Prosthesis | 17.62 | 27.91 | — |

|  | Vertical Translation (mm) | Vertical Slip (mm) | Rotational Slip (mm) |
| --- | --- | --- | --- |
| Original Socket Translation | 49.97 | — | — |
| Duplicate Prosthesis Translation | 49.76 | 2.31 | 2.83 |

Significant correlations ($p<0.01$) were found for both prostheses when comparing RL position to socket rotation, socket translation, and socket slip; and when comparing task weight to socket slip (FIG. 18). Significant correlations ($p<0.01$) were found for the Slip Detection Sensor prosthesis when comparing task weight to socket translation. The strongest correlations were found for task weight compared to socket slip and RL rotation compared to socket rotation as illustrated in FIG. 18.

Conclusion

Motion analysis and a SDS were used to record motions occurring at the socket interface. The results from each method were compared and show that socket rotations were dependent on the RL position, and the amount of socket slip was dependent on the loading of the terminal device for the tested tasks. Socket rotations have not previously been recorded using motion analysis, and this was the first implementation of the Slip Detection Sensor embedded in a prosthetic socket. This method allowed the participant to closely replicate how they would accomplish tasks in everyday living. The SDS provided additional information that could be useful in a dynamic interface system.

Example 2—Transtibial and Transfemoral Prostheses

A group of five veterans using a transtibial prosthesis and five using a transfemoral prosthesis are selected from the James A. Haley VA hospital (JAHVA). Subjects are consistent prosthesis users for at least one year and have had no documented skin or socket issues for the previous six months. A check socket is made for each subject and five slip detection sensors are placed in each socket. At the transtibial level, sensors are located over the tibial tubercle, the tibial shaft, the fibular head, the proximal gastrocnemius and the distal gastrocnemius. At the transfemoral level, sensors are placed over the trochanter, laterally proximal to the distal femur, medial superior, and anteriorly and posteriorly centered over the muscle bellies.

The inventors have obtained pliable shear sensors from Novel (Novel Electronics Inc., St. Paul, Minn., USA). These sensors are a new and emerging technology for measuring shear forces using a capacitive matrix. This technology works with their Pliance pressure mapping technology. These sensors are independent 1 cm×1 cm square shear sensors. These sensors connect to an interface box, which connects to the computer wirelessly via Bluetooth. Shear sensors are taped to the skin in locations corresponding to the slip locations described above.

Subjects are asked to walk back and forth along a 15 m long walkway. At the conclusion of testing, subjects are asked to assess the comfort of the socket using the Socket Comfort Score (SCS) and the Lower Extremity Functional Status of the Orthotic and Prosthetic Users Survey (OPUS).

Data Analysis

The primary analysis determines the correlation of shear and slip at each site individually at each sensor location and in the socket overall. Additionally, the comfort measures (SCS/OPUS) are expected to be inversely correlated with shear and slip. Finally, principal component analysis is used to identify the number and locations to place the slip detection sensors in the final design.

Example 3—Automated Socket Adjustment System

In developing the slip detection system, the optimal number and locations of Slip Detection Sensors was determined as well as determining a correlation between shear force and slip measurements.

The inventors use the results from the data collected to develop control algorithms to modify the socket over both short and long term utilizing various adaptive techniques. The inventors evaluate the system's ability to maintain socket fit given changes in residual limb volume by testing the dynamic socket system's ability to accommodate long term changes using a simulated residual limb and testing the effect of dynamic socket system on amputee comfort and user habits during the short term changes in residual limb.

The dynamic socket system continually monitors and detects changes in fit and the automated socket adjustment can advance residual limb health, increase prosthesis wear time, and improve overall socket performance. Measurements may be taken up to about 2.4 billion times per second. Further, the system may be used to determine when a greater adjustment or a new prosthetic socket is required. With regard to adjustment of the socket, algorithms receiving data from the sensor will constantly sample the multidirectional socket slip over time. Thresholds are programmed into the algorithm and if the amount of slip exceeds these limits then a signal is sent to the suspension system to increase/decrease the settings and automatically adjust the fit of the prosthesis.

The fit may be adjusted, for example in vacuum systems, by adding/releasing air automatically from the socket to improve fit. In this embodiment, the sensor may send a wireless or electrical signal to the processing unit on the actual vacuum system instructing the addition/release of air. An adjustment means such as a valve may be on the vacuum system to receive a wireless or electrical signal from the sensor to add or remove air.

In systems using mechanical members such as the Revolimb discussed previously, the system may have a motor or other device which is used to move the mechanical members to adjust fit. No commercial device currently exists to automate changes to the fit of the socket or warn the user when conditions are more likely to cause soft tissue damage.

With regard to the needed replacement of a socket system, continuously high sensor readings when the adjusting suspension system is at a maximum point, is indicative of a new socket being needed since it is likely that the limb has changed size.

The key to a successful dynamic interface is to incorporate feedback that is independent of the method of suspension. In existing prostheses, the socket is static or is maintained at a constant level, i.e. vacuum pressure. Current prosthetic design requires the user to be actively involved in diagnosing and adjusting the prosthesis on a regular basis. By providing active and automated adjustment based on feedback from the Slip Detection Sensor, the ability of the prosthesis to self-diagnose and adjust is improved, which in turn improves the comfort and fit of prosthesis, reduces the burden of the user to diagnose and adjust the prosthesis, and ultimately increases the functional lifespan of prosthetic devices.

Develop Control Algorithms to Modify the Socket Over Short and Long Term Utilizing Various Adaptive Techniques The optimal dynamic system has adjustable members, with locations based on the concept of skeletal stabilization advocated by Alley, herein incorporated into this disclosure in its entirety by reference. (Alley, R., *Biomechanical Discussion of Current and Emergent Upper-Limb Prosthetic Interface Designs*. The Academy Today, 2009. 5(3)) The adjustable members in this system are moveable panels within the socket wall, pneumatic or fluid-filled bladder system or vacuum system. These members may be located around the socket wall or at the distal end of the socket. In use, these members move in and out to control socket shape by providing more or less compression of the limb. The inner component is a flexible element consisting of flexible thermoplastic, silicone, or poly-tol (Ottobock, Duderstadt, Germany) or similar material. The soft interface preserves the long held concepts of total contact as well as the ability to provide suction suspension, while the adjustable members allow the dynamic control of socket shape. The Slip Detection Sensor is integrated into the control of these systems and sends a signal to the motor for mechanical systems or a wireless or electrical signal (if hardwired) for a vacuum system. Additionally, vacuum assisted suction may be used as an additional suspension. The Slip Detection Sensor also includes a programmable board which contains onboard memory and battery life for 2 weeks of uninterrupted use without recharging or downloading. A Bluetooth connection is also available to download the data at two week intervals.

Four to six expert users may be recruited from the James A. Haley VA Hospital (JAHVA). These subjects have a limb made incorporating active suspension elements and Slip Detection Sensors. These expert users return for each iteration of design for a brief evaluation. Each visit will consist of several walking trials, traversing the multiple terrain obstacles (Grass, Gravel Sand) in our gait and balance lab, outdoor walking and several user generated items. Expert user feedback includes comfort, ease of use, acceptability, noise, weight, and user perceptions.

Evaluate the System's Ability to Maintain Socket Fit Given Changes in Residual Limb Volume Simulated Testing Long Term Accommodation Given the difficulties in monitoring long term changes in the residual limb, the inventors have chosen to use a simulated model to simulate long term body fluid. A model residual limb is made incorporating a fluid bag filled with 250 ml of saline solution. The model and simulated socket with active system is attached to the Dynatup 9250HV (Instron, Norwood, Mass.) materials testing device. The limb is moved up and down cyclically with a maximum downward force equivalent to an 80 kilogram and an upward maximal force equivalent to the maximum shear force previously found. The cyclic movement is tested for 2700 cycles. After testing, 50 ml saline is removed from the model to simulate volume loss and the test is repeated. The test is repeated until +/−150 ml saline have been added or removed.

Subject Testing of Short Term Accommodations.

Subjects who have participated as expert users, as detailed above, are excluded from participation in this part of the research study. Subjects come into the research center and a prosthetic socket incorporating the new Slip Detection Sensors and adjustable components is fabricated. Initially, the Slip Detection Sensors are turned off. The physical therapist reviews volume management and prosthetic care.

Subjects are allowed to accommodate to the socket for two weeks. The amount of time required to accommodate to a new prosthesis is the subject of considerable debate, and appears to vary between users. Two weeks is generally considered to be sufficient. If the subject, therapist or prosthetist feel that accommodation period has been insufficient for a given subject, they may extend the duration of accommodation. After accommodation, the subject uses the prosthesis for two weeks with the Slip Detection Sensor turned off. During the two week period, subjects keep a log of daily performance including socket comfort scores, sock ply adjustments, and donning and doffing. Subjects then come into the lab for an evaluation including motion analysis and functional testing. At the conclusion of testing, the Slip Detection Sensor is turned on.

Subjects repeat the two weeks of at home use with log of SCS scores and return for the second gait analysis. Total limb volume and fat composition is measured at each visit. Limb volume is measured by water displacement and fat composition is measured with Futrex Infrared Body Composition Analyzer.

Data Analysis

The simulated long term testing is evaluated using ANOVA. Successful completion of the iterative phase is complete when the analysis shows no statistical difference in movement from +150 ml to −150 ml of volume change. Subject testing is done pre-post using the students' T test. The primary measure is socket comfort score.

Correlations between variables are evaluated post-hoc. Several of the measures correlate because sock ply adjustments, frequency of donning and doffing, and comfort are all elements of the same construct. Based on the differences found here, a power analysis is calculated to determine the sample size required to find significant difference in a future clinical trial.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A system configured to measure movement between a prosthetic socket and a residual limb as the residual limb moves within the prosthetic socket and distinguish between multidirectional socket slip, socket rotation, and soft tissue deformation comprising:
   - a prosthetic socket having an orifice positioned laterally in a socket wall;
   - an optoelectronic sensor positioned within a circular optical sensor port having an interior and an exterior wall and having open opposing ends wherein one end is embedded within the orifice in the socket wall of the prosthetic socket and the opposing end is attached to a lateral side of a housing wherein the interior wall of the circular optical sensor port encircles and is in contact with an exterior wall of the optoelectronic sensor;
   - a processing unit electrically connected to the optoelectronic sensor wherein the processing unit is configured to receive a set of feedback data from the optoelectronic sensor relating to the multidirectional socket slip, the socket rotation, and the soft tissue deformation wherein the processing unit contains software configured to analyze the feedback data and distinguish between and compare the multidirectional socket slip, the socket rotation, and the soft tissue deformation to a threshold;
   - a battery electrically connected to the processing unit;
   - a light emitting diode electrically connected to the battery and contained within the circular optical sensor port; and
   - a housing comprised of a base having a bottom, two sets of opposing lateral sides and a removeable top cover defining an interior compartment therein wherein the processing unit and the battery are contained within the interior compartment of the housing;
   - wherein the housing is positioned relative to the prosthetic socket such that the lateral side of the housing that is attached to the opposing end of the circular optical sensor port abuts an exterior surface of the socket wall to occlude the orifice positioned laterally within the socket wall when the circular optical sensor port is inserted into the orifice.

* * * * *